(12) United States Patent
Luo

(10) Patent No.: US 12,201,773 B1
(45) Date of Patent: Jan. 21, 2025

(54) PATIENT INTERFACE PAD WITH GOOD COMFORT AND ITS MANUFACTURING METHOD

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/416,130

(22) Filed: Jan. 18, 2024

(51) Int. Cl.
*A61M 16/06* (2006.01)

(52) U.S. Cl.
CPC . *A61M 16/0622* (2014.02); *A61M 2205/0216* (2013.01); *A61M 2207/00* (2013.01)

(58) Field of Classification Search
CPC ............ A41D 13/1176; A41D 13/1192; A61B 5/0826; A61F 13/2002; A61F 5/00; A61K 2800/10; A61K 2800/54; A61K 8/0208; A61K 8/895; A61L 31/06; A61L 31/10; A61L 31/146; A61M 11/00; A61M 16/0057; A61M 16/0066; A61M 16/0069; A61M 16/024; A61M 16/06; A61M 16/0605; A61M 16/0611; A61M 16/0616; A61M 16/0622; A61M 16/0633; A61M 16/0638; A61M 16/0644; A61M 16/065; A61M 16/0655; A61M 16/0666; A61M 16/0683; A61M 16/0688; A61M 16/0694; A61M 16/0816; A61M 16/0825; A61M 16/0833; A61M 16/0875; A61M 16/0891; A61M 16/10; A61M 16/1005; A61M 16/107; A61M 16/1075; A61M 16/1085; A61M 16/109; A61M 16/1095; A61M 16/12; A61M 16/16; A61M 16/161; A61M 16/20; A61M 16/208; A61M 16/209; A61M 2016/0027; A61M 2016/003; A61M 2016/0039; A61M 2016/0661; A61M 2202/0007; A61M 2202/0085; A61M 2202/0208; A61M 2202/0225; A61M 2202/30; A61M 2205/02; A61M 2205/0205; A61M 2205/0216; A61M 2205/0222; A61M 2205/0238; A61M 2205/0266; A61M 2205/15; A61M 2205/332; A61M 2205/3334; A61M 2205/3368; A61M 2205/3379;

(Continued)

(56) References Cited

U.S. PATENT DOCUMENTS

| 5,370,696 A * | 12/1994 | Jamison | B05D 1/10 128/898 |
| 2006/0207599 A1 * | 9/2006 | Busch | A61M 16/0622 128/206.24 |

(Continued)

*Primary Examiner* — Annette Dixon
(74) *Attorney, Agent, or Firm* — HSML P.C.

(57) ABSTRACT

A patient interface pad with good comfort, configured to supply pressurized gas to an airway, includes a support section, an elastic section, and a comfort section. The support section and the elastic section together form a complete patient interface pad; the material of the comfort section includes foam, fabric, or a composite of both; the comfort section has different three-dimensional shapes and is connected to the patient interface pad to form the patient interface pad; the disclosure also discloses a manufacturing method for the patient interface pad with good comfort, as well as the connection method between the comfort section and the patient interface pad which is through an adhesive.

16 Claims, 26 Drawing Sheets

(58) Field of Classification Search
CPC .. A61M 2205/3569; A61M 2205/3592; A61M 2205/3653; A61M 2205/42; A61M 2205/50; A61M 2205/581; A61M 2205/6054; A61M 2205/7527; A61M 2205/7536; A61M 2205/8206; A61M 2205/84; A61M 2207/00; A61M 2207/10; A61M 2209/02; A61M 2209/086; A61M 2210/0618; A61M 2210/0625; A61M 2230/432; A61M 2250/00; A61Q 19/00; A62B 18/08; B33Y 80/00; C08G 77/08; C08G 77/12; C08G 77/28; C08G 77/392; C08J 2207/10; C08J 2383/00; C08J 2383/08; C08J 9/00; C08L 41/00; C08L 43/04; C08L 83/08; Y10T 29/49; Y10T 29/49826

See application file for complete search history.

(56) References Cited

U.S. PATENT DOCUMENTS

| | | | |
|---|---|---|---|
| 2009/0223521 A1* | 9/2009 | Howard | A61M 16/0638 128/206.23 |
| 2014/0251338 A1* | 9/2014 | Asvadi | C08G 77/392 128/206.22 |

* cited by examiner

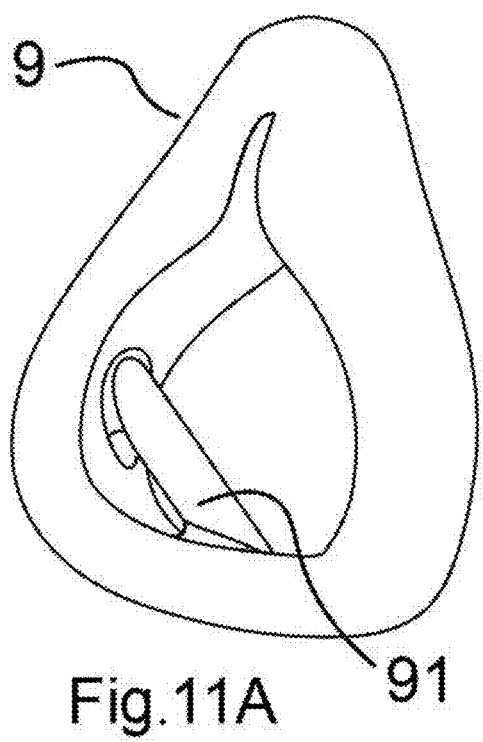 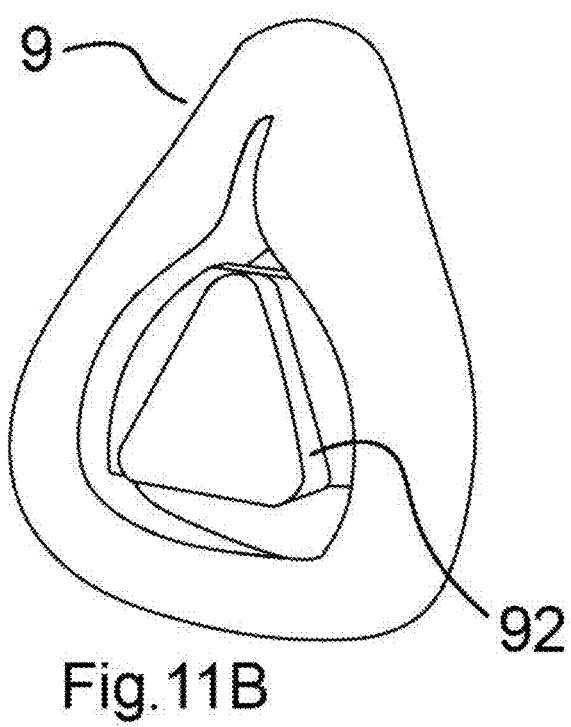
Fig.11A    91      Fig.11B    92

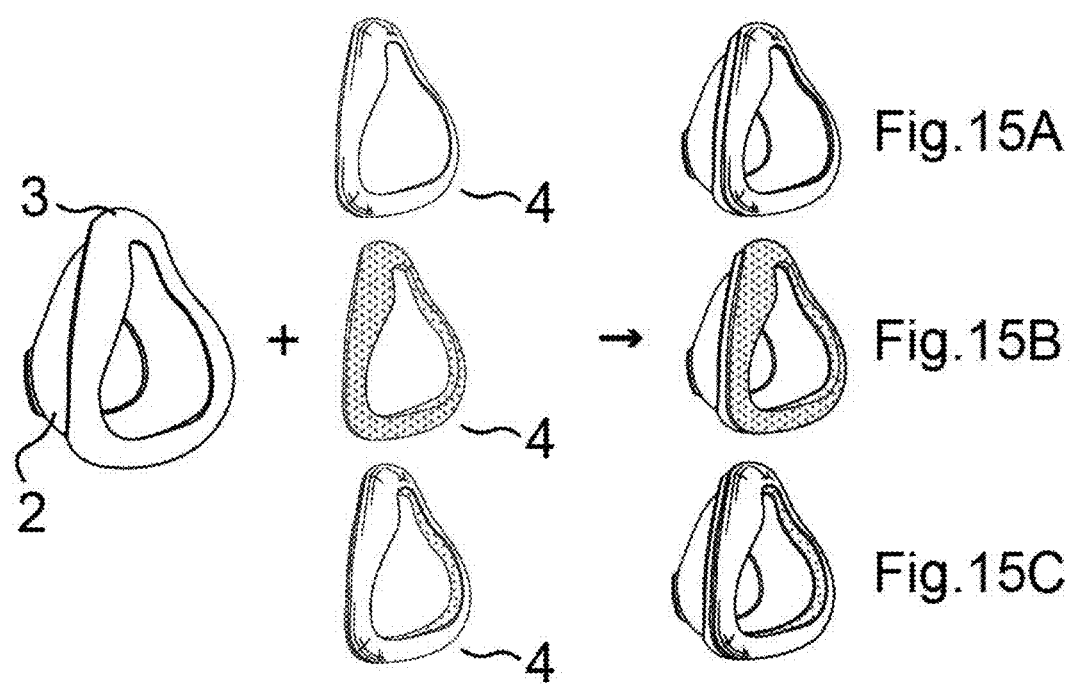

S1

S2

S2

S2

S7

PATIENT INTERFACE PAD WITH GOOD COMFORT AND ITS MANUFACTURING METHOD

TECHNICAL FIELD

This disclosure pertains to the field of patient interface pads, specifically to a patient interface pad for sealing the airway, and more specifically, it relates to a patient interface pad with good comfort and its manufacturing method.

BACKGROUND

Breathing is one of the key processes for maintaining vital signs, primarily aiming to achieve gas exchange through the function of the upper and lower respiratory tracts. However, some individuals repeatedly experience apneas and episodes of hypoventilation more than 30 times within 7 hours of nighttime sleep. Airway collapse prevents them from performing normal gas exchange, rendering the lungs unable to inhale sufficient oxygen and exhale carbon dioxide. This condition is known as Sleep Apnea Syndrome (SAS), also referred to as Sleep Apnea Hypoventilation Syndrome, where respiratory failure leads to a range of diseases and disorders. One of the methods for treating sleep apnea at home is CPAP (Continuous Positive Airway Pressure) therapy. Patients need to wear a corresponding device (patient interface assembly) connected to a machine that supplies pressurized air, providing them with sufficient pressurized air for breathing. However, designing the patient interface pad, which is part of the device, that contacts the face, presents numerous challenges: the human face, with its bones and the contour of soft tissues, has a complex three-dimensional shape that varies in structure, size, shape, and sensitivity from person to person. In recent years, due to the significant public health event of COVID-19, some people have experienced complications with respiratory difficulties, leading to an increase in the number of individuals with sleep apnea, which in turn has elevated the demand for patient interface pads.

Therefore, the design of patient interface pads not only needs to consider the basic requirements of sealing the airway and wearing comfort but also adaptability and flexibility to accommodate different patients. Additionally, it is important to consider how to quickly and massively produce various patient interface pads to meet the needs of different patients to the greatest extent possible.

SUMMARY

Therefore, to address the aforementioned shortcomings, it is necessary to provide a patient interface pad with good comfort and its manufacturing method.

In an embodiment, a patient interface pad with good comfort, configured to seal and deliver a pressurized airflow relative to the ambient air pressure to the entrance of an airway is provided. The patient interface pad includes at least some of the following elements or features. A support section includes a first opening and a second opening. The second opening is configured to connect to an elastic section. The elastic section includes a third opening connectable to the support section, a fourth opening opposite the third opening, and a side wall that connects the third opening and the fourth opening. Part of the side wall has a first surface, and the first surface is configured to connect to a comfort section; the comfort section includes a second surface in contact with the elastic section and a third surface that contacts a face. The comfort section includes foam material. The first surface of the elastic section and the second surface of the comfort section are connectable by an adhesive, and the adhesive has one or more of the following characteristics: an amount of the adhesive used is at least 0.05 g; b. a density range is at or between 0.3 to 3 $g/cm^3$; c. a temperature resistance range is at or between −55° C. to 200° C.; d. a tensile strength is greater than or equal to 0.5 MPa; e. a adhesive is applied in a continuous path and the perimeter of the path is not less than the perimeter of the fourth opening.

In an embodiment, the patient interface pad accommodates both a nasal airway and an oral airway, or only the nasal airway.

In an embodiment, the material of the support section is polycarbonate, polypropylene, polyethylene, or thermoplastic elastomer with a hardness of Shore A at or between 30 to 80, and the second opening of the support section and the third opening of the elastic section are connected and formed by molding or co-molding.

In an embodiment, the first surface of the elastic section and the second surface of the comfort section, when connected, have a same curvature in a part where they come into contact with each other, and the third surface of the comfort section partially conforms to a curve of the face during use.

In an embodiment, the foam material has a continuous three-dimensional shape with a width-to-thickness ratio at or between 0.1 to 30.

In another embodiment, a patient interface pad with good comfort configured to seal and deliver a pressurized airflow relative to the ambient air pressure to the entrance of an airway is provided. The patient interface pad includes at least some of the following elements or features. A support section includes a first opening and a second opening. The second opening is configured to connect to an elastic section. The elastic section includes a third opening connectable to the support section, a fourth opening opposite the third opening, and a side wall that connects the third opening and the fourth opening. Part of the side wall has a first surface, and the first surface is configured to connect to a comfort section. The comfort section includes a second surface in contact with the elastic section and a third surface that contacts a face. The comfort section includes fabric. The first surface of the elastic section and the second surface of the comfort section are connectable by an adhesive, and the adhesive has one or more of the following characteristics: a. an amount of the adhesive used is at least 0.03 g; b. a hardness is greater than or equal to Shore A 15; c. a density is at least 0.3 $g/cm^3$; d. a color after curing is transparent or translucent.

In an embodiment, the patient interface pad accommodates both a nasal airway and an oral airway, or only the nasal airway.

In an embodiment, the material of the support section is polycarbonate, polypropylene, polyethylene, or thermoplastic elastomer with a hardness of Shore A at or between 30 to 80, and the second opening of the support section and the third opening of the elastic section are connected and formed by molding or co-molding.

In an embodiment, the fabric is elastic, and changes in accordance with changes of a curvature of the elastic section when the fabric is subjected to pressure, and a roughness average value of the third surface of the comfort section is at or between 0.2 to 10 micrometers.

In an embodiment, an opening area of an inner edge of the fabric is not less than 23 $mm^2$.

In another embodiment, a patient interface pad with good comfort configured to seal and deliver a pressurized airflow relative to the ambient air pressure to the entrance of an airway is provided. The patient interface pad includes at least some of the following elements or features. A support section includes a first opening and a second opening. The second opening is configured to connect to an elastic section. The elastic section includes a third opening connectable to the support section, a fourth opening opposite the third opening, and a side wall that connects the third opening and the fourth opening. Part of the side wall has a first surface, and the first surface is configured to connect to a comfort section. The comfort section includes a second surface in contact with the elastic section and a third surface that contacts a face. The comfort section includes foam material and fabric. The second surface of the comfort section includes foam material, and the third surface includes fabric, with the foam material and fabric being in a connected state. The first surface of the elastic section and the second surface of the comfort section are connectable by an adhesive, and the adhesive has one or more of the following characteristics: a. an amount of the adhesive used is at least 0.05 g; b. a density is at most 3 g/cm$^3$; c. a temperature resistance range is at or between −55° C. to 200° C.; d. an adhesive is applied in a continuous path and a perimeter of the path is not less than a perimeter of the fourth opening. In an embodiment, the patient interface pad accommodates both a nasal airway and an oral airway, or only the nasal airway.

In an embodiment, the material of the support section is polycarbonate, polypropylene, polyethylene, or thermoplastic elastomer with a hardness of Shore A at or between 30 to 80, and the second opening of the support section and the third opening of the elastic section are connected and formed by molding or co-molding.

In an embodiment, the first surface of the elastic section and the second surface of the comfort section, when connected, have a same curvature in a part where they come into contact with each other, and the third surface of the comfort section partially conforms to a curve of the face during use.

In an embodiment, the foam material has a continuous three-dimensional shape with a width-to-thickness ratio at or between 0.1 to 30.

In an embodiment, the fabric is elastic, and changes in accordance with changes of a curvature of the elastic section when the fabric is subjected to pressure, and a roughness average value of the third surface of the comfort section is at or between 0.2 to 10 micrometers.

In an embodiment, the foam material is connectable to the fabric by the adhesive, or through an intermediate layer, and the intermediate layer includes thermoplastic polyurethane material.

In another embodiment, a manufacturing method for a patient interface pad with good comfort is provided. The patient interface pad has a support section, an elastic section, and a comfort section. The comfort section is connectable to the elastic section by an adhesive. Steps of the manufacturing method are as follows: step S1, obtaining the elastic section connectable to the support section, and the corresponding comfort section, and cleaning the elastic section as well as the comfort section; step S2, applying the adhesive manually or automatically to a portion of either the first surface of the elastic section or the second surface of the comfort section; step S3, connecting the elastic section, which has been coated with the adhesive, to the comfort section accordingly, so that the adhesive is placed between the elastic section and the comfort section, step S4, letting the patient interface pad which has the comfort section after connection set aside, waiting for the adhesive to cure; the adhesive has one or more of the following characteristics: a. an amount of the adhesive used is at least 0.03 g; b. a hardness after curing is greater than or equal to Shore A 15; c. a perimeter of the path where the adhesive is applied is not less than the perimeter of a fourth opening of the elastic section; d. an area where the adhesive is applied does not exceed a second surface of the comfort section; e. a colloidal state before curing is liquid or semi-flowing.

In an embodiment, the patient interface pad accommodates both a nasal airway and an oral airway, or only the nasal airway.

In an embodiment, the comfort section includes foam material and fabric. The foam material is connectable to the fabric using an adhesive or through an intermediate layer, and the intermediate layer includes thermoplastic polyurethane material.

In an embodiment, the steps are completed through a cooperation of a first container and a second container, and the first container is a fixture that secures the patient interface pad, and the second container is a fixture that secures the comfort section.

In another embodiment, a manufacturing method for a patient interface pad with good comfort is provided. The patient interface pad has a support section, an elastic section, and a comfort section. The comfort section is connectable to the elastic section by an adhesive. Steps of the manufacturing method are as follows: step S1, obtaining the elastic section connectable to the support section, and the corresponding comfort section, and cleaning the elastic section as well as the comfort section; step S2, applying the adhesive manually or automatically to a portion of the second surface of the elastic section; step S3, connecting the elastic section to the comfort section correspondingly, letting the adhesive sit between the elastic section and the comfort section. step S4, letting the patient interface pad which has the comfort section after connection set aside, waiting for the adhesive to cure. The adhesive has one or more of the following characteristics: a. an amount of the adhesive used is at least 0.03 g; b. a hardness after curing is greater than or equal to Shore A 15; c. a perimeter of the path where the adhesive is applied is not less than the perimeter of a fourth opening of the elastic section; d. an area where the adhesive is applied does not exceed a second surface of the comfort section; e. a colloidal state before curing is liquid or semi-flowing.

In an embodiment, the patient interface pad accommodates both a nasal airway and an oral airway, or only the nasal airway.

In an embodiment, the comfort section includes foam material and fabric. The foam material is connectable to the fabric using an adhesive or through an intermediate layer, and the intermediate layer includes thermoplastic polyurethane material.

In an embodiment, the steps are completed through a cooperation of a first container and a second container, and the first container is a fixture that secures the patient interface pad, and the second container is a fixture that secures the comfort section.

Implementing the patient interface pad and its manufacturing method in the disclosure provides at least the following beneficial effects:

1. Reduced R&D Cycle: Most patient interface pads on the market, aiming to provide a more comfortable user experience for patients, focus on researching and designing the curvature of the elastic section to better conform to the curves of the face. Due to the complex three-dimensional characteristics of the human face, the design process requires reference to a large amount of ergonomics-related data. This involves extensive testing, verification, and adjustments for comfort and airtightness. Furthermore, the production of the elastic section, owing to the material's curing requirements, typically has a longer production cycle compared to the supportive parts. In this approach, a. R&D personnel need to create a three-dimensional model of the patient interface pad. Based on this established three-dimensional model, they proceed with mold making (this process typically takes 30 to 50 days). Only after obtaining the mold can the production of the elastic section begin. b. Due to the elastic section typically being made of thermoplastic elastomer materials, its production involves several steps: preparation of raw materials (usually supplied in pellet form), pre-treatment (the material needs to experience pre-treatment steps of drying and mixing of raw materials to ensure the quality and stability of material), injection of raw materials (using the prepared mold for injection molding), and cooling and curing treatment (curing time often takes several days). c. The research and development personnel need to conduct numerous comfort and air-tightness tests on the produced products, then adjust the three-dimensional models, and repeat these steps multiple times to develop a patient interface pad with good comfort. The preparation method of this disclosure uses the same patient interface pad, and connects different materials to the elastic section of the patient interface pad, through the research and the design of more readily obtainable materials which are comfortable and capable of deformation such as foam material (foam molding) and fabric (textile process). This approach shortens the design process for optimizing the comfort of the patient interface pad, thereby realizing a faster provision of a more comfortable experience for the patient. In this method, a. Prepare a patient interface pad suitable for the facial shape of the majority of people in the early stage, and at the same time, design comfortable materials, and produce a variety of forms of the comfort section through relatively simple operations such as cutting and trimming the comfortable materials. b. Connect the patient interface pad with the comfort section by adhesive through a fix connection and then multiple types of patient interface pads contacting different areas of the user's face can be obtained. By producing patient interface pads with varying degrees of comfort in this way, it is possible to eliminate redesign steps in the production of thermoplastic elastomers, reducing research and development time by three months or more. Additionally, it enables the rapid design of new types of the comfort section based on market trends or user preferences, allowing the patient interface pads to meet the comfort needs of different patients, therefore, the product can be put on the market more quickly and effectively, by creating a series of products.

2. Modular Preparation Method: In the current patient interface pad market, most patient interface pads are configured to match with a fixed frame component to form a complete patient interface assembly for use. However, these interface pads cannot meet the needs of different patients. For producers, designing different patient interface pads within the same patient interface assembly is undoubtedly a waste of cost: a. It requires producing support sections with the same function but different structures, wasting materials; b. The elastic sections are usually made of thermoplastic elastomers, which typically have slower production times and higher defect rates than materials like plastic. Considering these two points, the optimized design of patient interface pads demands high requirements in terms of material costs and time costs. In the preparation method of this disclosure, a modular approach is used. Innovatively, comfortable materials like foam material and fabric are fixedly connected to the patient interface pad. This method allows for the provision of a variety of patient interface pads with good comfort for the market. a. Producers only need to manufacture one universal patient interface pad, eliminating the need to waste materials on multiple design validations of the elastic section for air-tightness and comfort. b. In this manufacturing method, since the more complex parts of the product (the support section and the elastic section) are confirmed, it is only necessary to design different types of the comfort section to meet patient needs. This approach makes quality control of the components easier, stabilizes the overall product quality control, and saves overall production time. It also significantly reduces the defect rate. c. The support section and the elastic section, as the basic parts of the patient interface pad, have increased reusability, which can reduce the adverse environmental impact of excessive industrial products.

3. Supply Aspect: Currently, the supply of ordinary patient interface pads in the market, from the perspective of the product supply chain, requires warehouses to be equipped with different types of patient interface pads to meet the varying needs of different patients for shipment, which demands high storage costs (material costs, space costs, etc.). For the product suppliers, factories need to be equipped with different types of production molds for patient interface pads to prepare the relatively complex patient interface pads, resulting in high costs in terms of mold expenses and material consumption. In the face of major public health events such as COVID-19, there has been a huge challenge to the supply of medical materials. The production cycle of ventilators, which is already not short, has faced a global shortage. This has led to a widespread situation of demand outstripping supply among ventilator manufacturers. The reason lies in the numerous materials and processes required for ventilator systems, with the majority of raw materials being in short supply due to the obstacles caused by the pandemic. By using a modular design approach, a. Producers only need to prepare one model for producing patient interface pads and store a large number of the same patient interface pads in the warehouse. During the preparation and assembly of goods, products can be quickly shipped out by fixing the comfort section to the elastic section of the patient interface pad with adhesive according to customer needs. This significantly reduces storage and production costs, reduces material waste, and enhances the flexibility of the production line; and uses simpler, more readily available materials, without the need for extensive imports or special materials, to ensure the stability of the supply chain. b. In this manufacturing method, since there are many fundamentally similar parts in the product, the same production processes, tools, and equipment can be adopted, which reduces production and manufacturing costs. Different modular components can be manufactured simultaneously and can undergo independent testing and inspection. This allows for quick repairs of components that encounter a problem, making quality control of the components easier. It stabilizes the overall product quality control, saves time in overall production, and significantly reduces the defect rate. c. The support section and the elastic section, as the foundational parts of the patient interface pad, have increased reusability, which can reduce the adverse environmental impact of excessive industrial products. d. Materials like foam material and fabric, compared to thermoplastic elastomers, are easier to shape into the desired form, allowing for quicker iterations in the product supply.

4. Providing Users with Better Patient Interface Pads: Besides offering users a variety of patient interface pads, more importantly: a. Compared to existing patient interface pads that use silicone seals alone, fabric, foam material, or their composite are more breathable than silicone. They can provide varying degrees of comfortable contact surfaces. Additionally, they can absorb oils and sweat produced during prolonged use, keeping the face dry and avoiding skin sensitivity issues, as well as reducing the displacement of silicone because of contact with sweat or oils. b. The adhesive used in this method is non-toxic and harmless, with moderate tensile strength, appropriate softness and hardness after curing, and it is transparent or semi-transparent after curing. Furthermore, adhesive does not damage the surface of the elastic section or produce harmful waste. c. Due to lower production costs, the purchasing cost for patients is also reduced, making it more affordable for users. Users are able to enjoy and experience a wider variety of patient interface pads, allowing them to choose the most suitable one.

BRIEF DESCRIPTION OF THE DRAWINGS

FIG. 11A and FIG. 11B are schematic diagrams of the support element in the manufacturing method of a patient interface pad with good comfort in accordance with an embodiment;

FIG. 15A, FIG. 15B and FIG. 15C are schematic diagrams showing various embodiments of the comfort section in a patient interface pad with good comfort in accordance with an embodiment;

DETAILED DESCRIPTION

To make the objectives, features, and advantages of this disclosure more apparent and understandable, the specific embodiments of the disclosure are described in detail in conjunction with the accompanying drawings. Many specific details are set forth in the following description to provide a thorough understanding of the disclosure. However, this disclosure can be implemented in many other ways different from those described here, and those skilled in the art can make similar improvements without violating the essence of the disclosure. Therefore, this disclosure is not limited by the specific embodiments disclosed below.

This disclosure aims to solve the problems of traditional patient interface pads using silicone to contact a face, which is not breathable and causes the face to easily become oily and sweaty, leading to displacements of the common patient interface pads and affecting the seal. It also addresses issues like mask liners and mask covers that easily wrinkle and are uncomfortable to wear. A patient interface pad with good comfort is provided, using fabric 5, foam material 6, or composite of both 7 to fit the user's face, which can absorb sweat and oil and is more breathable, making the wearer's experience more comfortable, alleviating the distress of undergoing treatment, easing the user's mindset during treatment, and resulting in better compliance. It also provides specific manufacturing steps for the rapid production of this comfortable patient interface pad.

The following describes a patient interface pad with good comfort and its manufacturing method of the disclosure, in conjunction with specific embodiments.

Embodiment 1

Figure 1:
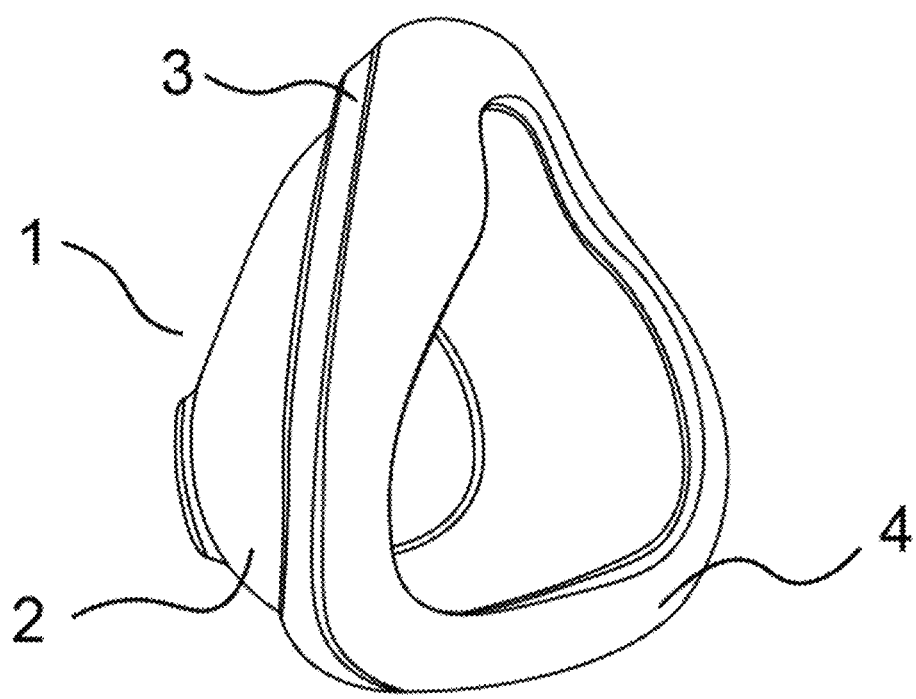
FIG. 1 is a schematic diagram of the structure of a patient interface pad with good comfort in accordance with an embodiment.

The objective of this disclosure is to provide a patient interface pad with good comfort, which is configured to deliver a pressurized airflow relative to the ambient air pressure to the entrance of an airway. As shown in FIG. 1, the patient interface pad includes a support section 2, an elastic section 3, and a comfort section 4.

Figure 2:
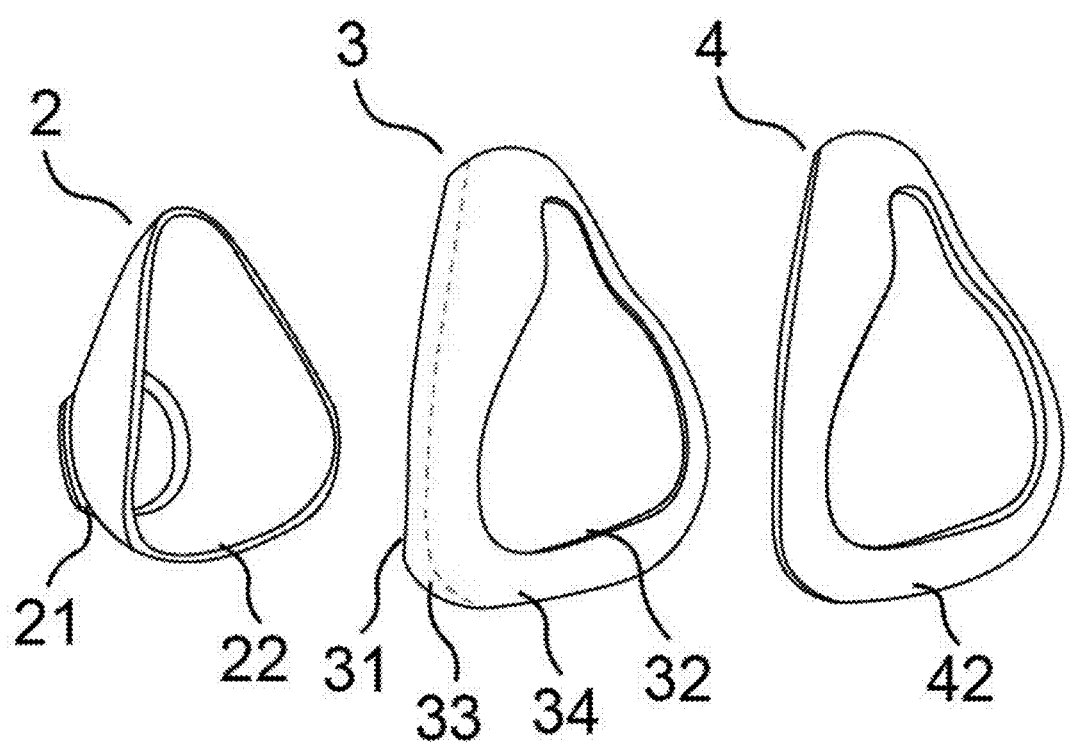
FIG. 2 is an exploded structural schematic of a patient interface pad with good comfort in accordance with an embodiment.

Specifically, as shown in FIG. 2, the support section 2 is used to support the elastic section 3 and includes a first opening 21 and a second opening 22. The first opening 21 is configured to contact other parts of the patient interface assembly (such as elbows, frames, etc.) and, for added comfort and flexibility during patient use, is typically a fixed circular interface with a diameter at or between 10 to 45 mm (in other embodiments, it can be of other shapes). The second opening 22 is configured to connect to the elastic section 3, together forming a chamber to contain the pressurized airflow. The connection between them can be made through molding, co-molding, or other non-detachable methods, or through detachable methods like snap-fits or magnetic attraction. The support section 2 preferably uses rigid materials for better support of the elastic section 3, such as polycarbonate, polyethylene, polypropylene, or thermoplastic elastomers with a hardness of Shore A at or between 30 to 80.

Figure 8:
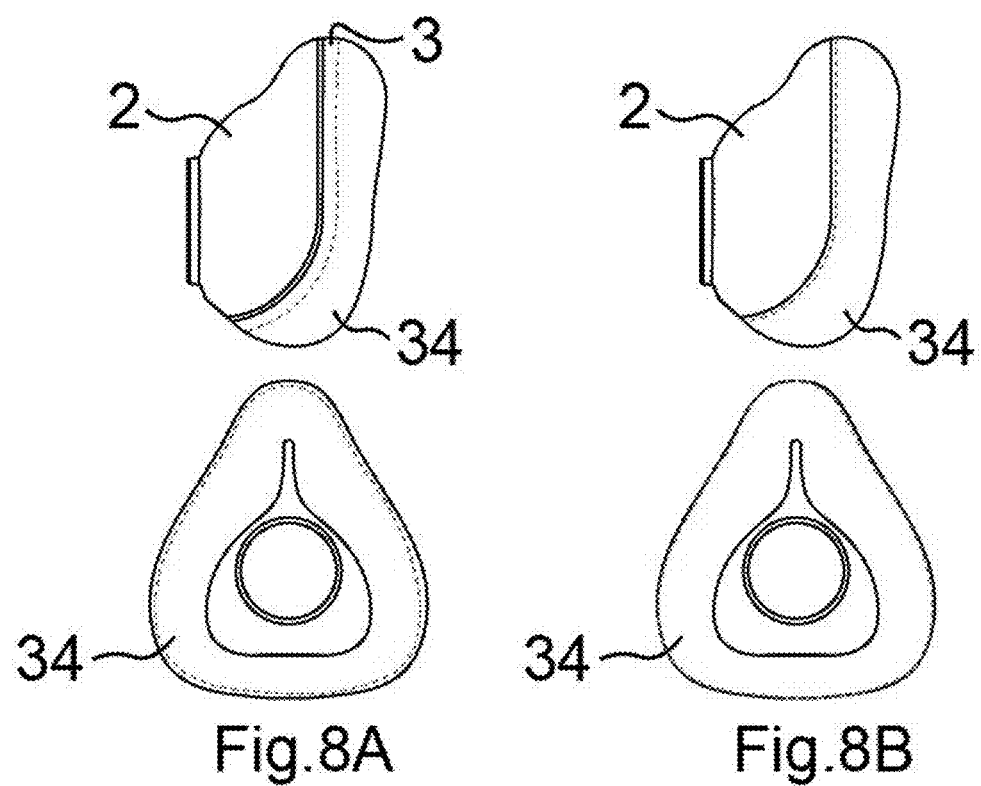
FIG. 8A and FIG. 8B are schematic diagrams showing the area of adhesive application in the manufacturing method of a patient interface pad with good comfort in accordance with an embodiment.

The elastic section 3 is used to connect to the support section 2 and provide attachment points for the comfort section 4. The elastic section 3 includes a third opening 31 that connects to the support section 2, an opposite fourth opening 32, and a side wall 33 that connects the third opening 31 and the fourth opening 32. The fourth opening 32 is configured to accommodate the nasal and oral airways. As shown in FIG. 8, for the elastic section to better provide attachment for the comfort section 4, part of the side wall 33 has a relatively gentle first surface 34. The first surface 34 is configured to connect to the comfort section 4 by adhesive 8. As shown in FIG. 8A, in this embodiment, the outer edge of the comfort section 4 can be connected to the elastic section 3. As shown in FIG. 8B, in this embodiment, the outer edge of the comfort section 4 can be connected to the connection area of the elastic section 3 and the support section 2. The elastic section 3 is softer and more deformable than the support section 2, able to conform to facial deformations. The elastic section is typically made of flexible materials with a hardness of Shore A at or between 30 to 70, such as silicone, rubber, or other thermoplastic elastomers, preferably using biocompatible materials with a hardness between Shore A at or between 35 to 50. To make the patient interface pad 1 more comfortable and durable, the wall thickness of the elastic section 3 can be single-layered, multi-layered, or non-uniform. Generally, the part of the elastic section 3 that connects to the support section 2 is thicker than the other parts (the rest parts which exclude the connecting part of the elastic section 3), making it more robust and less prone to breaking. The fourth opening 32 can be thinner than other parts (excluding the remainder of the fourth opening 32), allowing for greater deformation capability to adapt to the facial contours of different patients, better conforming to the skin, and enhancing the overall air-tightness of the patient interface pad 1.

Figure 3:
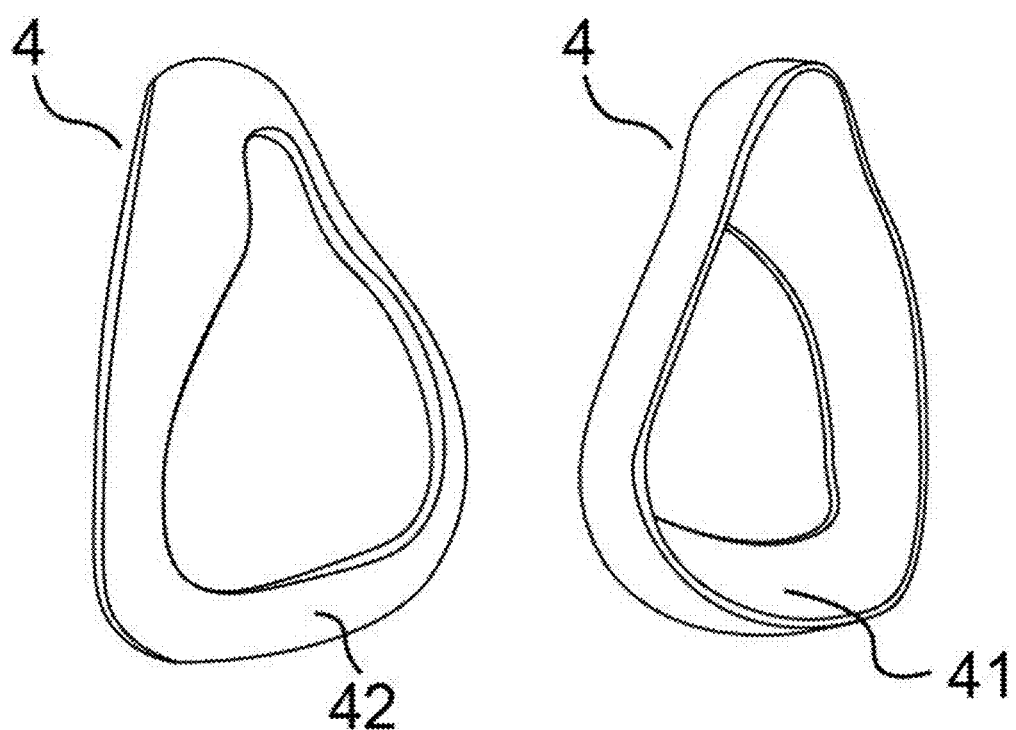
FIG. 3 is a three-dimensional schematic diagram of the comfort section of a patient interface pad with good comfort in accordance with an embodiment.

Specifically, as shown in FIG. 3, the comfort section 4 includes a second surface 41 in contact with the elastic section 3 and a third surface 42 for contacting the face. The second surface 41 is securely connected to the first surface 34 of the elastic section 3 by adhesive 8. In the common contact portion, the second surface 41 of the comfort section 4 and the first surface 34 of the elastic section 3 can have the same curvature (i.e., the same shape, contour, and undulation), or they can have different curvatures (i.e., the second surface 41 can be flat or have other curvatures).

Figure 4:
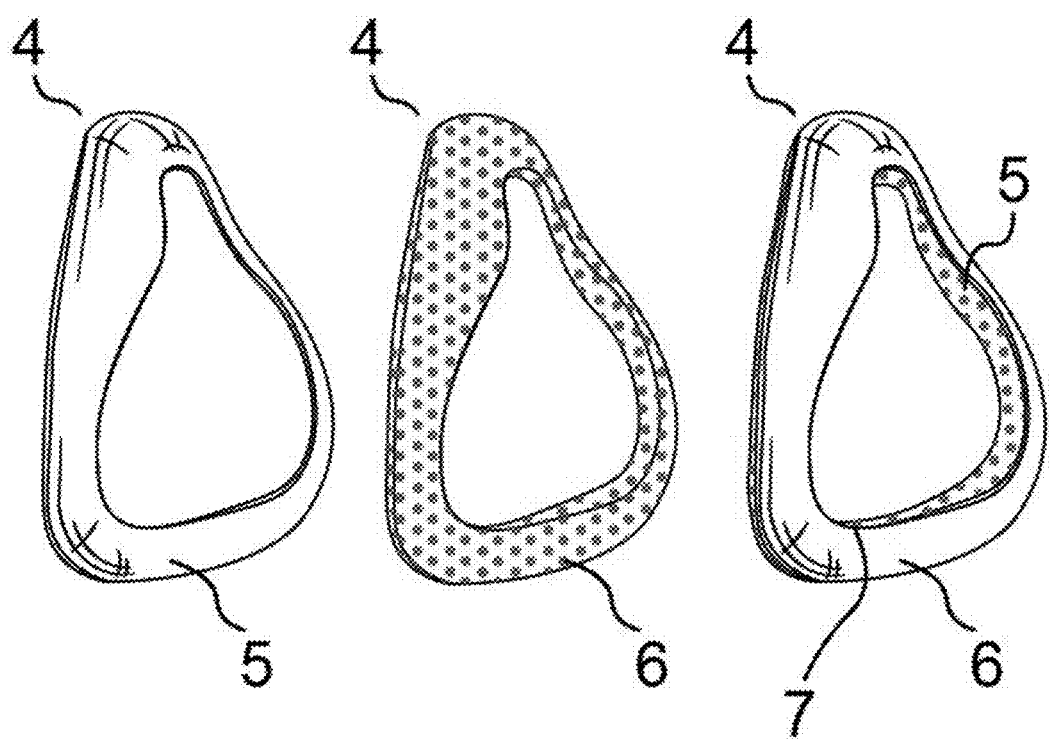
FIG. 4 is a schematic diagram of different materials for the comfort section of a patient interface pad with good comfort in accordance with an embodiment.

To achieve a more comfortable adaptation experience and enhance the overall airtightness of the patient interface pad 1, the third surface 42 of the comfort section 4 can be configured into a three-dimensional contour with different characteristic undulations based on the requirements of respiratory assistance equipment and user needs. The third surface 42 can partially conform to the curvature of the facial features. As shown in FIG. 4, the comfort section 4 is more fluffy, soft, and breathable compared to the elastic section 3 and can be made of foam material 6, fabric 5, or a composite of both 7. The comfort section 4 has a general teardrop shape with an inner edge and an outer edge. The inner edge shape can be roughly triangular, elliptical, teardrop-shaped, or another shape that can accommodate the nasal passage and oral passages.

Figure 26:
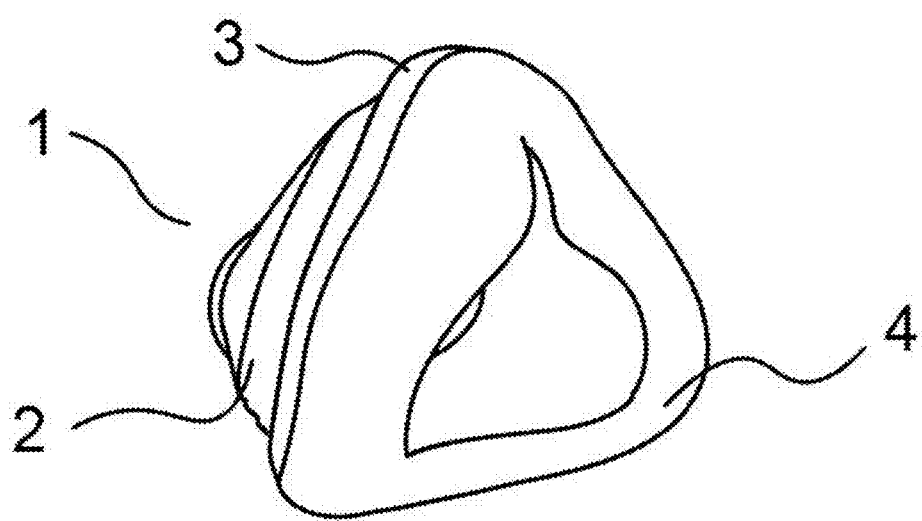
FIG. 26 is a schematic diagram of the structure of a patient interface pad with good comfort in accordance with an embodiment.

In other embodiments, as shown in FIG. 26, the fourth opening 32 of the elastic section 3 can be used to accommodate only the patient's nasal airway, i.e., in conjunction with the comfort section 4 and the nasal mask. The fourth opening 32 of the elastic section 3 can be used to accommodate only the nasal airway, that is, the comfort section 4 is used in conjunction with a nose mask.

In other embodiments, the support section 2 and the elastic section 3 can be made of the same material, such as in smaller invasive nasal masks, all using materials such as silicone, rubber, or other thermoplastic elastomers with a hardness of Shore A at or between 30 to 70.

Figure 9:
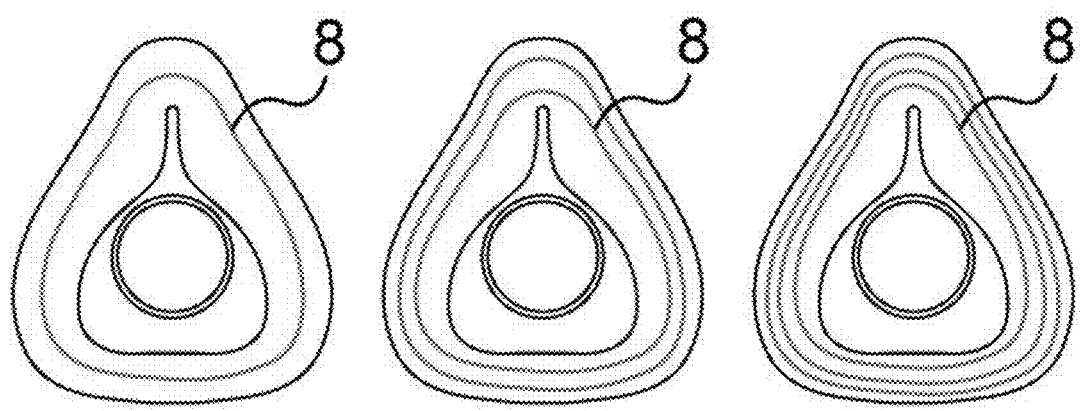
FIG. 9 is a schematic diagram showing the path of adhesive application in the manufacturing method of a patient interface pad with good comfort in accordance with an embodiment.
Figure 10:
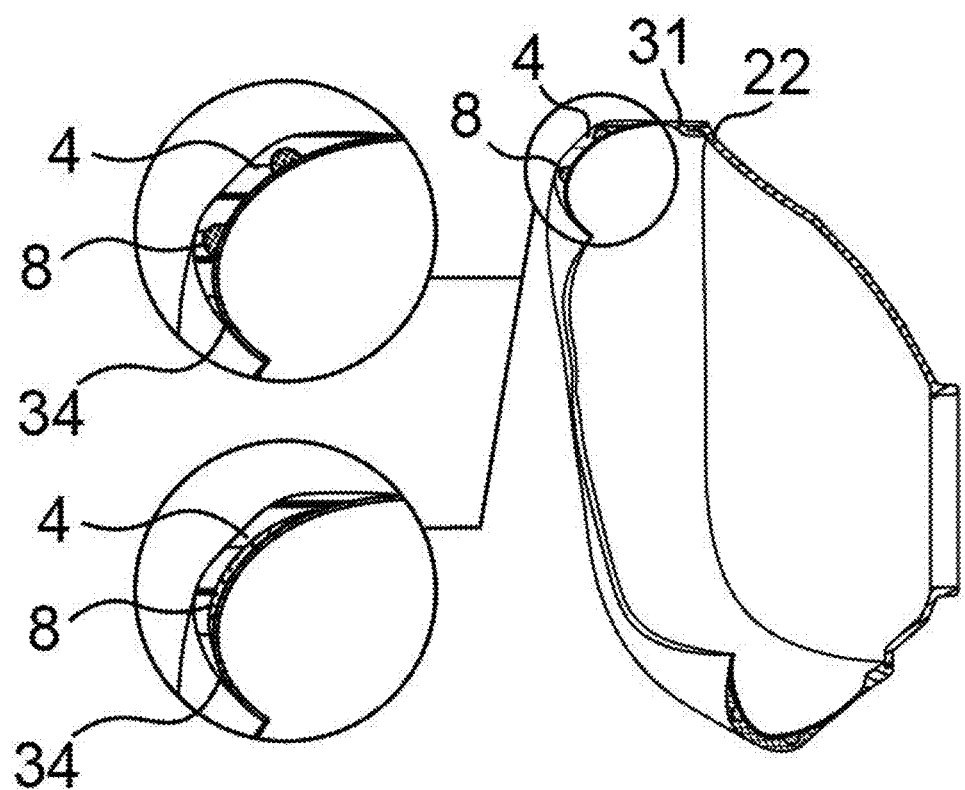
FIG. 10 is a schematic diagram showing the adhesive bonding site in the manufacturing method of a patient interface pad with good comfort in accordance with an embodiment.
Figure 12A:
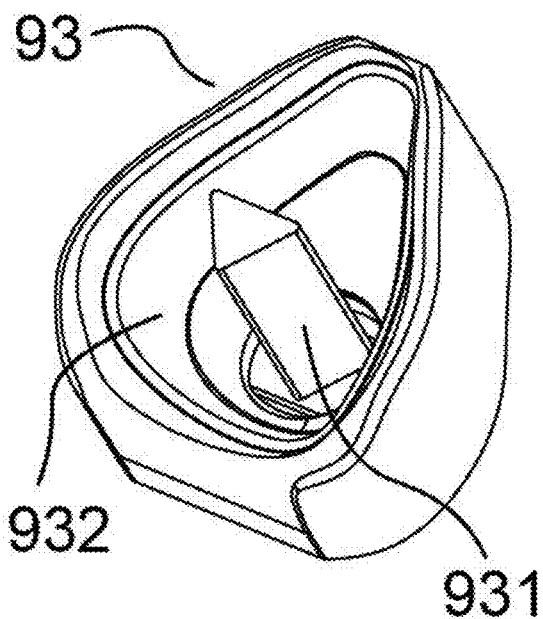
FIG. 12A and FIG. 12B are schematic diagrams of the fixture structure in the manufacturing method of a patient interface pad with good comfort in accordance with an embodiment.
Figure 13:
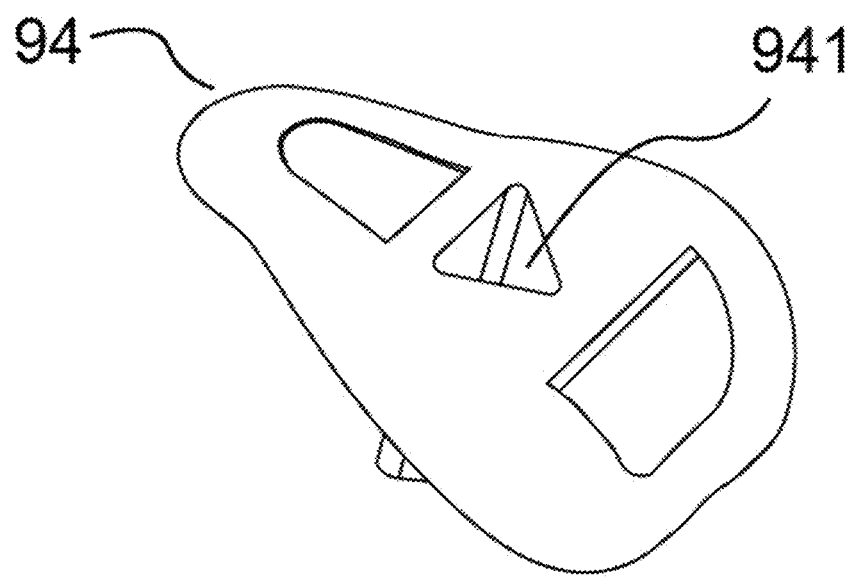
FIG. 13 is a schematic diagram of the fixture structure in the manufacturing method of a patient interface pad with good comfort in accordance with an embodiment.
Figure 14A:
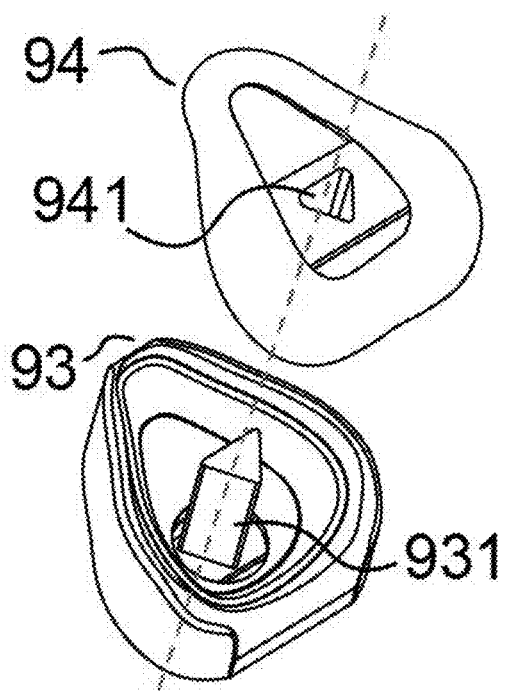
FIG. 14A and FIG. 14B are schematic diagrams showing the cooperation of the fixture in the manufacturing method of a patient interface pad with good comfort in accordance with an embodiment.
Figure 14B:
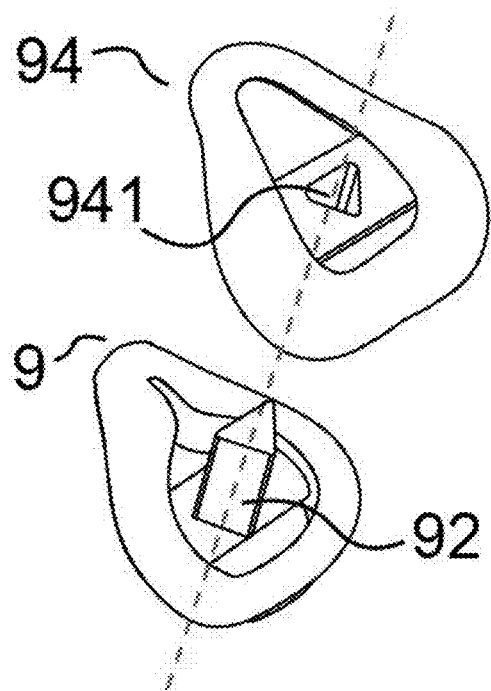
Figure 16:
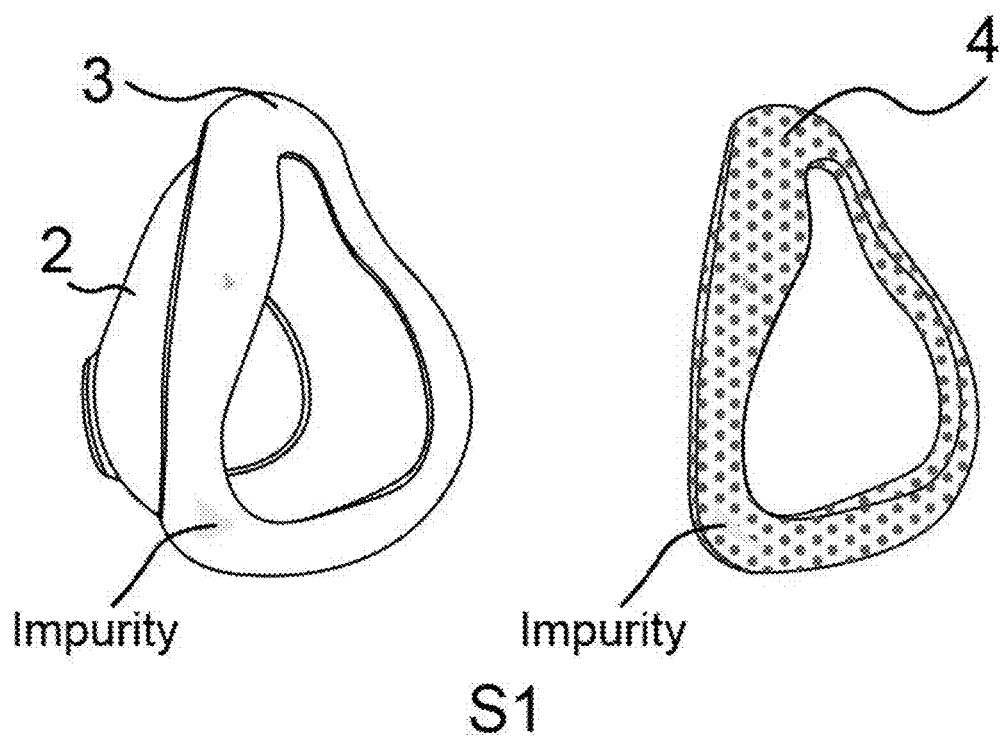
FIG. 16 is a schematic diagram of the manufacturing method steps S1 and S2 of a patient interface pad with good comfort in accordance with an embodiment.
Figure 17:
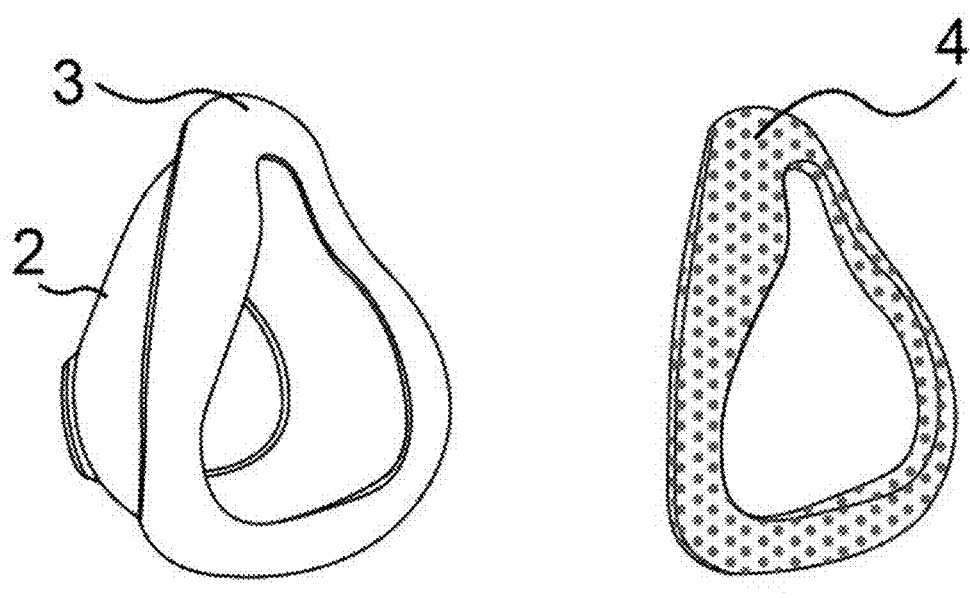
FIG. 17 is a schematic diagram of the manufacturing method step S3 of a patient interface pad with good comfort in accordance with an embodiment.
Figure 18:
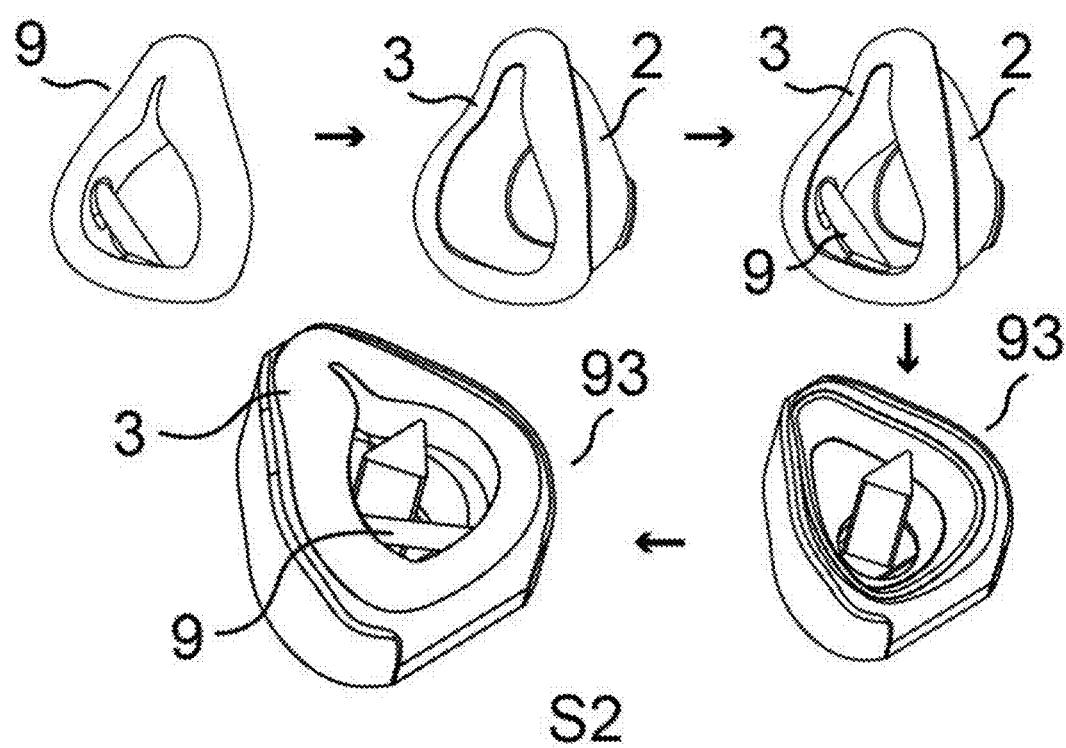
FIG. 18 is a schematic diagram of the manufacturing method step S4 of a patient interface pad with good comfort in accordance with an embodiment.
Figure 19:
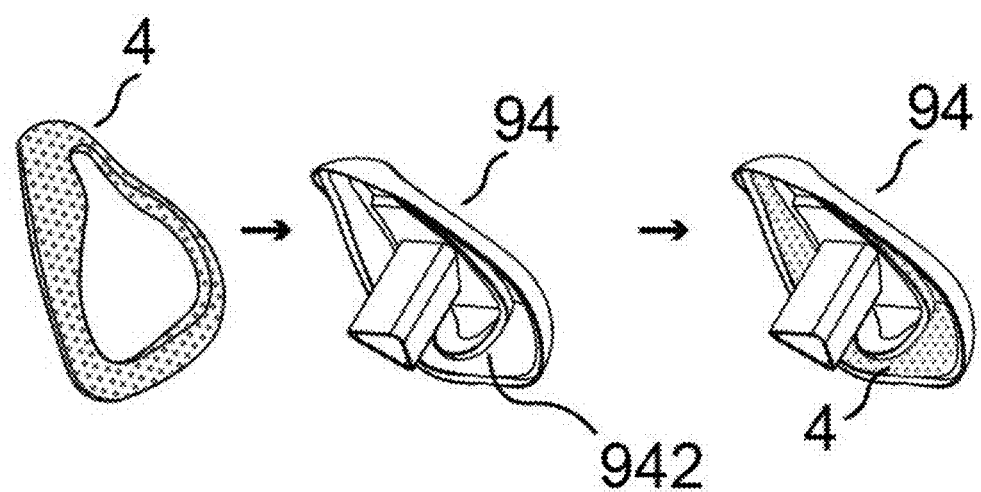
FIG. 19 is a schematic diagram of the manufacturing method step S5 of a patient interface pad with good comfort in accordance with an embodiment.
Figure 20A:
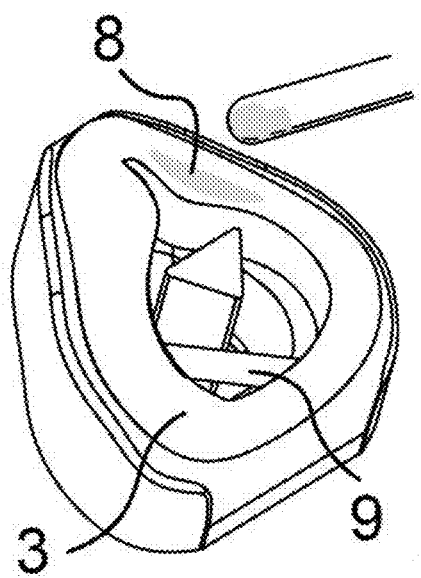
FIG. 20A and FIG. 20B are schematic diagrams of the manufacturing method step S6 of a patient interface pad with good comfort in accordance with an embodiment.
Figure 20B:
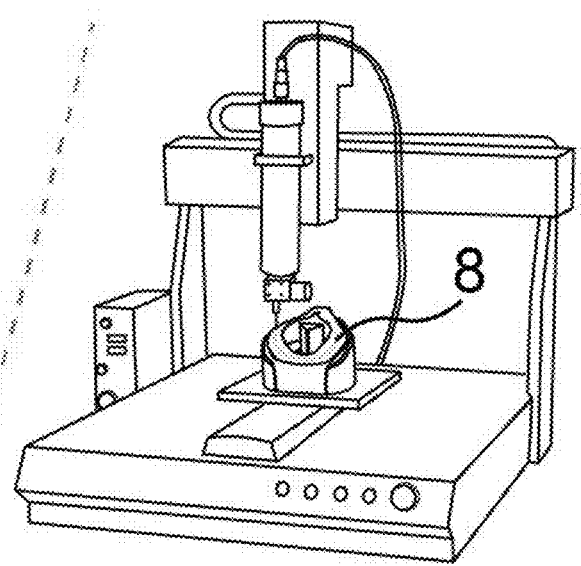
Figure 21:
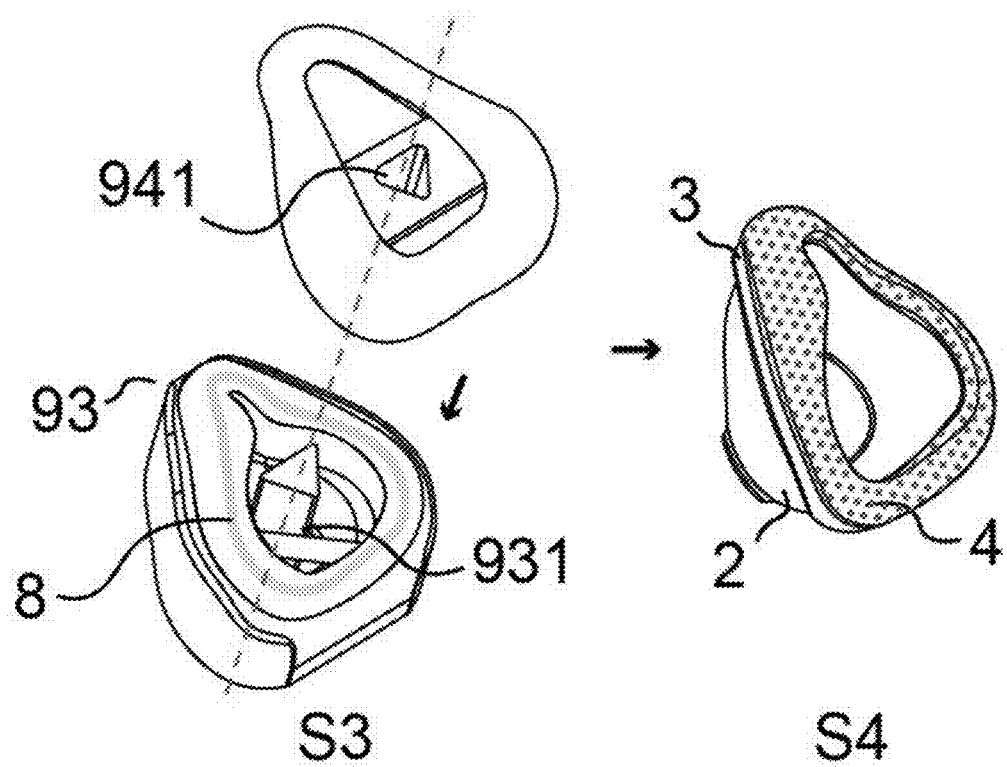
FIG. 21 is a schematic diagram of the manufacturing method step S7 of a patient interface pad with good comfort in accordance with an embodiment.
Figure 22:
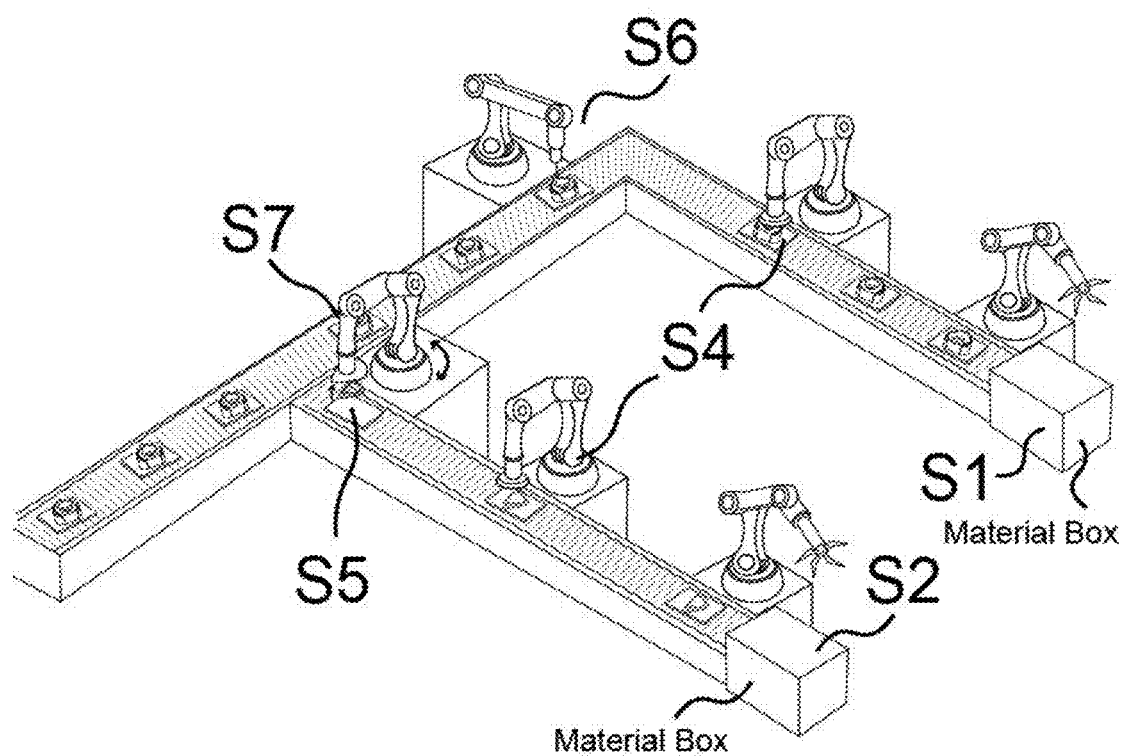
FIG. 22 is a schematic diagram of the automated manufacturing method steps of a patient interface pad with good comfort in accordance with an embodiment.
Figure 23:
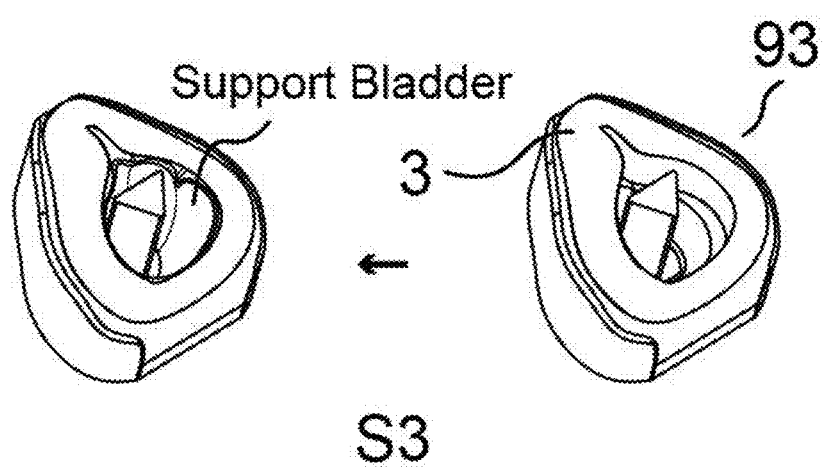
FIG. 23 is a schematic diagram of the automated manufacturing method step S3 of a patient interface pad with good comfort in accordance with an embodiment.
Figure 24:
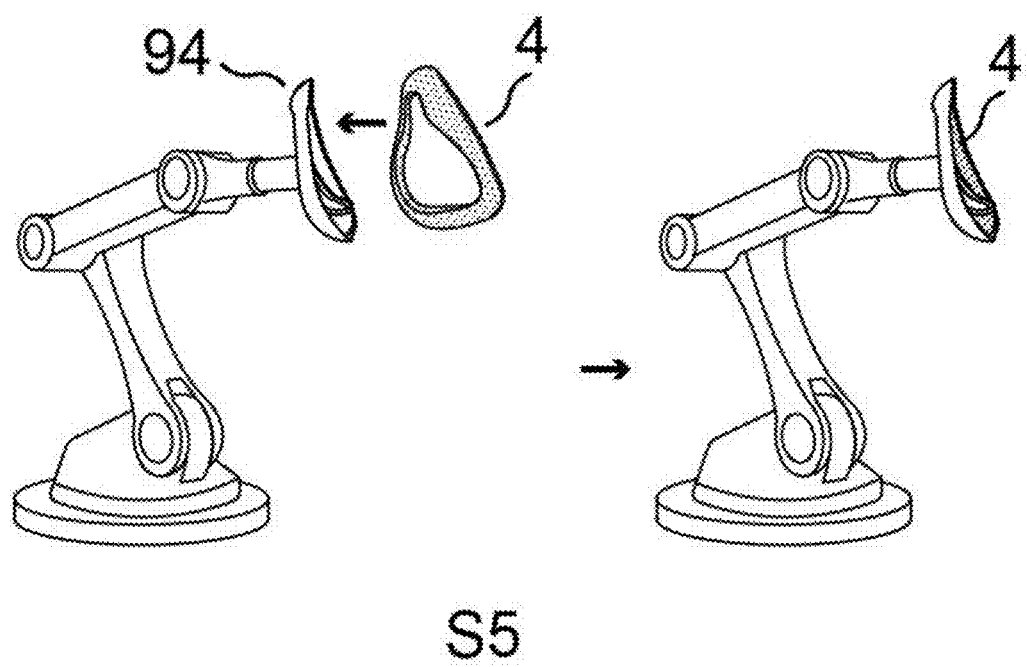
FIG. 24 is a schematic diagram of the automated manufacturing method step S5 of a patient interface pad with good comfort in accordance with an embodiment.
Figure 25:
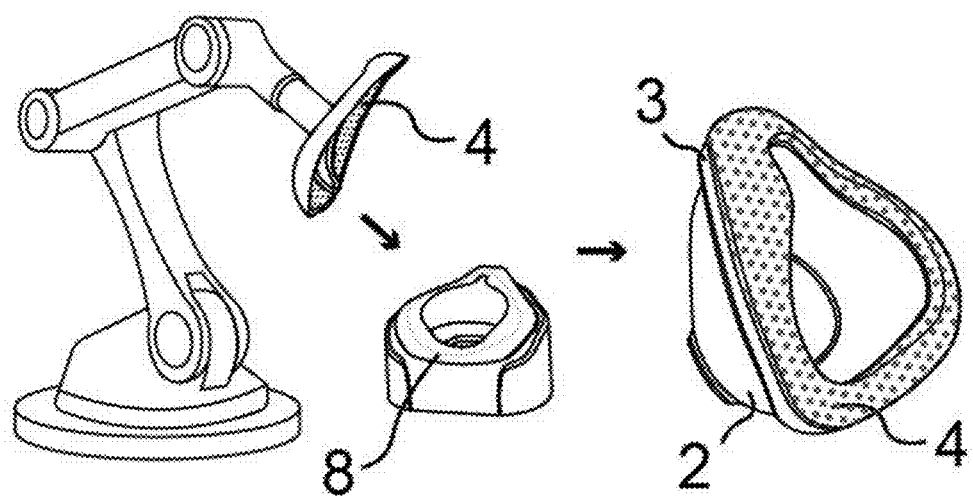
FIG. 25 is a schematic diagram of the automated manufacturing method step S7 of a patient interface pad with good comfort in accordance with an embodiment.

This embodiment provides a manufacturing method for making a patient interface pad with good comfort. Specifically, as shown in FIGS. 11-21, it includes the following steps:

Step S1, firstly, based on ergonomics data and numerous comfort and air-tightness tests, obtain the patient interface pad of the elastic section 3 (the elastic section 3 having an opening that meets the facial requirements of the patient) connected to the support section 2 (at this stage, the patient interface pad only having the support section 2 and the elastic section 3). The support section 2 includes a first opening 21 and a second opening 22, where the second opening 22 is configured to connect to the elastic section. They can be connected in a detachable or non-detachable manner. The first opening 21 is a fixed circular interface for connecting with external auxiliary devices (such as elbows, frames, etc.), and in other embodiments, it can be of other shapes. The elastic section 3 includes a third opening 31 connected to the support section 2, an opposite fourth opening 32, and a side wall 33 connecting the third and fourth openings. The fourth opening 32 can encircle the nasal airway or/and oral airway. Part of the side wall 33 of the elastic section 3 has a relatively gentle first surface 34. Secondly, according to the size and shape of the first surface 34 of the elastic section 3 of the obtained patient interface pad, form the corresponding size and shape of the second surface 41 of the comfort section 4, and determine the size and shape of the third surface 42 of the comfort section 4 that contacts the face, based on the requirements of the respiratory assistance device. In this disclosure, patient interface pads with the same support section 2 and elastic section 3 can be connected to different comfort sections 4 (the first surface 34 of the elastic section 3 is configured to be connected to the comfort section 4, which has a generally similar contour shape, or to the comfort section 4 with a different material than the third surface 42, through adhesive 8). On the other hand, to achieve a close fit of the comfort section 4 with the face, the third surface 42 of the comfort section 4 forms a continuous curved surface corresponding to the face during connection. When the first surface 34 of the elastic section 3 and the second surface 41 of the comfort section 4 are connected, the part they touch together has the same curvature. To ensure the stability of the part where the elastic section 3 and the support section 2 are connected, the wall thickness of the third opening 31 of the elastic section 3 is at least partly greater than that of the fourth opening 32. Then, perform the pretreatment of cleaning to the patient interface pad (elastic section 3) and comfort section 4 to ensure that the surfaces to be bonded are clean and tidy, free of oil stains, dust, wrinkles, and other contaminants that could affect the quality of adhesion;

Step S2 is completed through the cooperation of the first container and the second container, where the first container is fixture 93 that secures the support section 2 and the elastic section 3, and the second container is fixture 94 that secures the comfort section 4. The specific steps are as follows: First, place a support piece 9 inside the patient interface pad that has finished the pretreatment of cleaning, and fix the patient interface pad and support piece 9 in the first container. The first container can be fixture 93, as shown in FIG. 12A. The first container includes a receiving part 932 for the support section 2 or/and the elastic section 3 of the patient interface pad, and a positioning part 931 that connects to the second container. The support piece 9 is configured to provide support for the elastic section 3, as shown in FIG. 11A. The external contour of the support piece 9 is the same as the external contour of the elastic section 3. To achieve more stable support, the material of the support piece 9 is harder than that of the elastic section 3. The support piece 9 also features a handle part 91 for easy assembly and handling. Next, the comfort section 4, which has finished the pretreatment of cleaning, is fixed in the second container. The second container can be fixture 94, as shown in FIG. 13. The second container includes a receiving part 942 for holding the comfort section 4 and a positioning part 941 that connects to the first container. Then, adhesive 8 is applied manually or automatically to a portion of the first surface 34 of the elastic section 3. In this process, adhesive 8 is manually applied to a part of the first surface 34 of the elastic section 3 or fully covers the first surface 34. As shown in FIGS. 9-10, alternatively, the adhesive can be automatically applied by designing a program to a glue dispensing machine to follow a specific path. The dispensing path of the glue dispensing machine is a complete and continuous ring, and the number of paths can be chosen based on the material of adhesive 8, and at least one path can be chosen. Regardless of the method used, the range of adhesive 8 application does not exceed the second surface 41 of the comfort section 4. The application path is continuous, and the perimeter of the path is not less than the perimeter of the fourth opening 32;

Step S3, connect the first container and the second container according to their corresponding structures, let the adhesive 8 place between the elastic section 3 and the comfort section 4;

Step S4, let the patient interface pad which has the comfort section after connection set aside, wait for the adhesive 8 to cure.

In another embodiment, in Step S2, the adhesive 8 is applied manually or automatically to a portion of the second surface 41 of the comfort section 4. The adhesive 8 can be manually applied to a part of the second surface 41 of the comfort section 4 or entirely cover the second surface 41. It can also be applied automatically by programming a glue dispensing machine to follow a specific path. The dispensing path of the machine is a complete and continuous ring, with the number of paths being at least one, chosen based on the material of adhesive 8. The range of the adhesive 8 application does not exceed the second surface 41 of the comfort section 4.

Figure 12B:
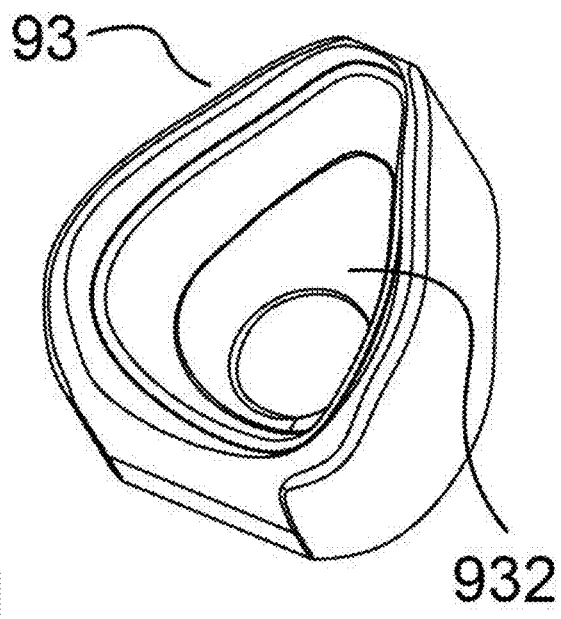

In another embodiment, as shown in FIGS. 11B, 12B, and 13, the first container can be fixture 93. The first container contacts the support section 2 of the patient interface pad or/and the receiving part 932 of the elastic section. The second container can be fixture 94, and the second container includes receiving part 942 which contacts the comfort section 4, and positioning part 941 which connects to the support piece 9. The support piece 9 is configured to support the elastic section 3 and connect to the second container. The support piece 9 includes positioning part 92 which connects to the second part. The external contour of the support piece 9 matches the external contour of the elastic section 3, and to achieve more stable support, the material of the support piece 9 is harder than that of the elastic section 3.

Adhesive 8 is typically chosen to be glue. To ensure the bonding quality and performance between the comfort section 4, the elastic section 3, and adhesive 8, and to avoid damage to the appearance and characteristics of the material of the comfort section 4 by the adhesive 8, as well as hardening or whitening after the adhesive 8 cures, attention should be paid to the following factors in the selection of the adhesive material: 1) Bonding strength: to ensure a sufficiently firm connection between the elastic section 3 and the comfort section 4, the use of adhesive 8 should be at least 0.03 g. This ensures, without the influence of the external force, that the connection force between the comfort section 4 and the elastic section 3 is greater than the gravitational pull of the comfort section 4 itself. Further, the patient interface pad does not fall off due to movement during sleep, without causing wrinkles that could lead to air leakage. 2) Material properties: The adhesive 8, being in proximity to the respiratory tract and face when the product is in use, should meet basic criteria: non-toxicity, odorlessness and other non-hazardous properties for human beings. After curing, it should be transparent or semi-transparent in color, to avoid leaving marks that affect the final appearance of the patient interface pad. The compatibility and adaptability between adhesive materials should be ensured, avoiding, during the bonding process, delamination, damage to material surfaces, chemical reactions that change material characteristics, or permeation. The adhesive 8 should be non-toxic, adaptable, and comply with local regulatory requirements, such as the ISO 10993 regulations. When used, adhesive 8 is in a liquid or semi-flowing state (in another embodiment, adhesive 8 is applied manually or automatically to a part of the second surface 41 of the comfort section 4, where it is in a semi-flowing state during use). The specific conditions depend on the materials the adhesive 8 contacts. After curing and setting, adhesive 8 should avoid exerting pressure on the user's face and adhesive 8 should not process a hardness that is greater than the hardness of the elastic section 3. The hardness of adhesive 8 after curing should be greater than or equal to Shore A 15. To prevent, when the patient interface pad undergoes deformation, the occurrence of breakage due to insufficient tensile strength of adhesive 8, or to prevent the adhesive 8's impact on the deformation of the patient interface pad, the tensile strength of the cured adhesive 8 should be greater than or equal to 2 MPa. At the same time, attention should be paid to whether adhesive 8 will penetrate the comfort section 4 when adhesive 8 is initially in a fluid state. If it permeates to the third surface 42 of the comfort section 4, it can affect the softness and breathability of the comfort section 4, making it feel stiff and uncomfortable for the user. 3) Environmental friendliness: Adhesive 8 should be chosen for its longer lifespan to avoid the rapid aging of the product. For protecting the environment, preferably, the adhesive 8 should be environmentally friendly and easily degradable, with energy saving, waste disposal, and process optimization all taken into comprehensive consideration. Adhesive from brands like 3M, Loctite, UHU, etc., can be chosen. In this embodiment, the chosen adhesive has the following basic characteristics: a density at or between 0.3 to 3 $g/cm^3$, a temperature resistance range at or between $-55°$ C. to $200°$ C., and a tensile strength greater than or equal to 0.5 MPa.

Embodiment 2

Figure 5:
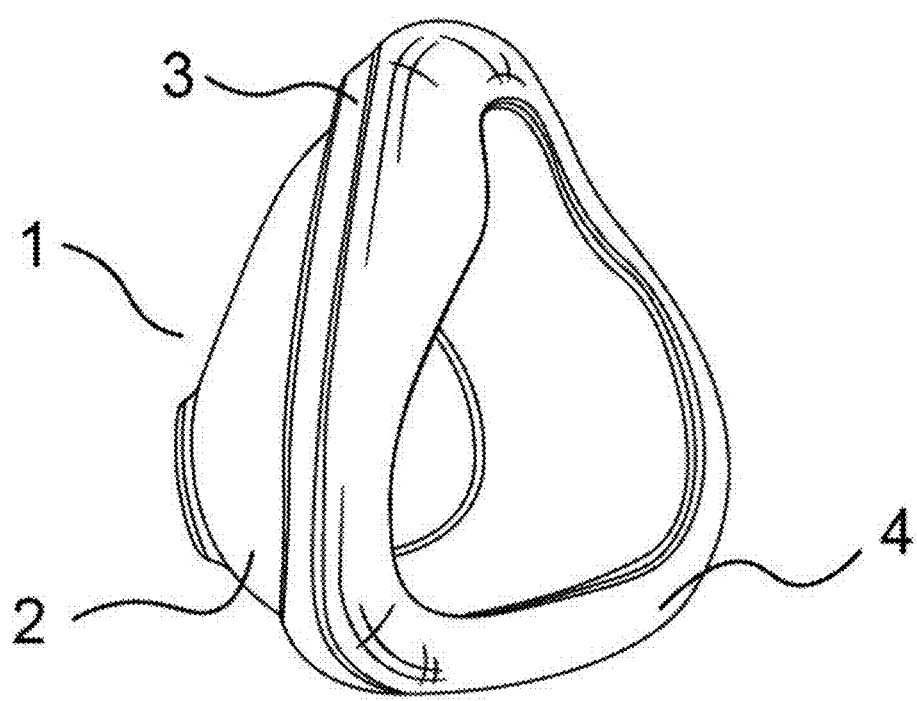
FIG. 5 is a schematic diagram of the structure of a patient interface pad with good comfort in accordance with an embodiment.

This embodiment describes a patient interface pad with good comfort, configured to deliver a pressurized airflow relative to the ambient air pressure to the entrance of an airway. The patient interface pad includes: a support section 2, including a first opening 21 in contact with other parts in the patient interface assembly (e.g., an elbow, an frame, etc.), connected to an elastic section 3; the elastic section 3, including a third opening 31 connected to the support section 2, a fourth opening 32 opposite the third opening 31, and a sidewall 33 that smoothly connects the third opening 31 and the fourth opening 32; and a comfort section 4, including a second surface 41 in contact with the elastic section 3 and a third surface 42 in contact with the face of the patient. Part of the side wall 33 of the elastic section 3 has a relatively gentle first surface 34 and the first surface is configured to be connected to the comfort section 4 through adhesive 8. The fourth opening 32 is configured to accommodate the nasal and oral airways or solely the nasal airway. The difference in this embodiment of the patient interface pad with good comfort from the patient interface pad in Embodiment 1 lies in: in this embodiment, the comfort section 4 is specifically limited as being made of fabric 5 (textile). As shown in FIG. 5, the fabric 5 of the comfort section 4 has the advantages of being absorbent and highly breathable. It can effectively absorb the facial secretions at night, keeping the face dry and breathable, and enhancing the compliance with the patient interface pad. The components of fabric are made of one following material or a combination of two or more of the following materials in different proportions and the materials are selected from cotton, silk, velvet, nylon, nylon, spandex, and polyester. Some fabrics 5 can also be made with metal fibers to create different functional fabrics 5, such as antibacterial fabrics or antistatic fabrics. Fabric 5 should have a permeability rate at or between 1 to 30 CFM (according to the air permeability test method in ASTM D737-18). In another embodiment, the air permeability is at or between 40 to 60 CFM, or at or between 50 to 80 CFM, to ensure patient comfort while avoiding excessive gas leakage. Fabric 5 should have a water absorption time of less than 30 seconds, preferably the water absorption time being less than 20 seconds, and more preferably the water absorption time being less than 10 seconds, to ensure it can absorb sweat and oil from the face. The count of fabric 5 should be no less than 30 and no more than 100, and the average roughness (Ra value) of the third surface 42 that contacts the face should be at or between 0.2 to 10 micrometers, ensuring fabric 5 provides a soft, comfortable surface for the patient and avoiding excessive pressure on the face due to the weight of fabric 5. Fabric 5 can be cut into a ring-shaped contour using methods such as laser, punching, cutting, or ultrasonics. The inner and outer edge shapes can be approximately triangular, oval, teardrop-shaped, circular, or any other shape that can cover the first surface 34 of the elastic section 3. The outer edge may be similar to the inner edge contour or similar to the general contour of the first surface 34. The opening area of the inner edge of fabric 5 should not be less than 23 $mm^2$. The first surface 34 of the elastic section 3 and the second surface 41 of the comfort section 4 (fabric 5) may have the same curvatures or different curvatures in their joint contact part. Fabric 5 is elastic and changes its shape according to the change of the curvature of the elastic section 3 when the fabric 5 is subjected to pressure. The third surface 42 of the comfort section 4 (fabric 5) conforms to the contours of the face. When the inner edge opening is less than or equal to the fourth opening 32 of the elastic section 3, it means that at this time, at least a part of the outer surface (contact area) of fabric 5 is sealed against the user's face. When the inner edge opening is greater than the fourth opening 32 of the elastic section 3 or the outer edge is smaller than the first surface 34 of the elastic section 3, it means that both the elastic section 3 and at least a part of the second surface 41 of fabric 5 simultaneously seal against the user's face. Fabric 5 can be in a single-layer form or a multi-layer form. The combination of multi-layer fabric 5 can be achieved through pressing, sewing, thermoplastic composites, or hot melt composites, and film composites. To ensure the sealing effectiveness of the patient interface pad, the thickness of fabric 5 is approximately at or between 0.8 mm to 3.5 mm (fabrics 5 that are too thin can easily lose elasticity and softness, while fabrics 5 that are too thick can easily shift and leak). The thickness of fabric 5 can be uniform or varied, such as gradually thinning towards the outer edge to conform to the elastic section 3, or thinning towards the inner edge to reduce the presence on the face. This embodiment provides a method for manufacturing a patient interface pad with good comfort. The difference from the patient interface pad in Embodiment 1 lies in the amount of adhesive 8 being used. To ensure that adhesive 8 does not completely penetrate fabric 5 during production and can tightly bond with the elastic section 3, at least 0.03 g of adhesive 8 is used.

Embodiment 3

This embodiment describes a patient interface pad with good comfort, configured to deliver a pressurized airflow relative to the ambient air pressure to the entrance of an airway. The patient interface pad includes: a support section 2, including a first opening 21 in contact with other parts in the patient interface assembly (e.g., an elbow, an frame, etc.), connected to an elastic section 3; the elastic section 3, including a third opening 31 connected to the support section 2, a fourth opening 32 opposite the third opening 31, and a sidewall 33 that smoothly connects the third opening 31 and the fourth opening 32; and a comfort section 4, including a second surface 41 in contact with the elastic section 3 and a third surface 42 in contact with the face of the patient. Part of the side wall 33 of the elastic section 3 has a relatively gentle first surface 34 and the first surface is configured to be connected to the comfort section 4 through adhesive 8. The fourth opening 32 is configured to accommodate the nasal and oral airways or solely the nasal airway. The difference in this embodiment of the patient interface pad with good comfort from the patient interface pad in Embodiment 1 lies in: the comfort section 4 is specifically limited as being made of foam material 6.

Figure 6:
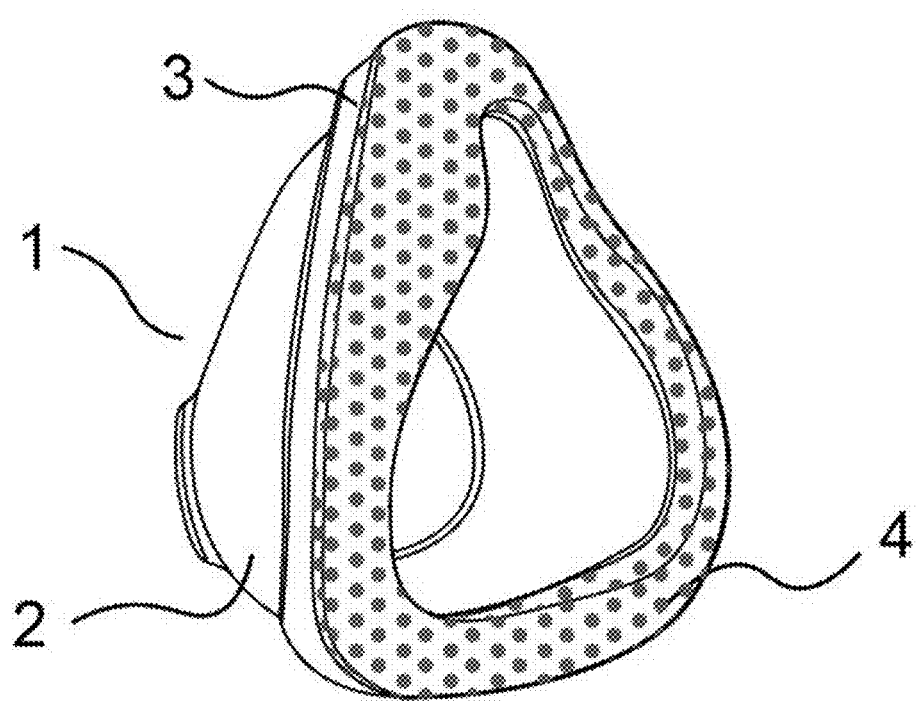
FIG. 6 is a schematic diagram of the structure of a patient interface pad with good comfort in accordance with an embodiment.

As shown in FIG. 6, the foam material 6 is a porous material, including but not limited to polyurethane foam, ethylene-vinyl acetate foam, latex, and other soft, elastic materials, with a density at or between 10 to 100 kg/m$^3$. The permeability of foam material 6 is less than 50 L/min, ensuring that the patient interface pad bonded with foam material 6 does not affect the overall air-tightness. Part of foam material 6 has a three-dimensional shape (in another embodiment, foam material 6 has a continuous three-dimensional shape), with a width at or between 3 to 30 mm, and a width-to-thickness ratio at or between 0.1 to 30. The cross-section of foam material 6 can be approximately quadrilateral, pentagonal, hexagonal, and for better comfort, the edges of the first surface 34 will be set in an arc treatment. The third surface 42, which contacts the face, conforms to the curvature of the face. During wear, the elastic section 3 and the comfort section 4 conform to the contours of the face and deform to varying degrees, approximately fitting the shape of the face, dispersing facial pressure, and achieving a more comfortable wearing experience.

This embodiment provides a method for manufacturing a patient interface pad with good comfort. The difference from the patient interface pad in embodiment 1 lies in the amount of adhesive 8 being used. To ensure that adhesive 8 does not completely penetrate fabric 5 during production and can tightly bond with the elastic section 3, at least 0.05 g of adhesive 8 is used.

Embodiment 4

Figure 7:
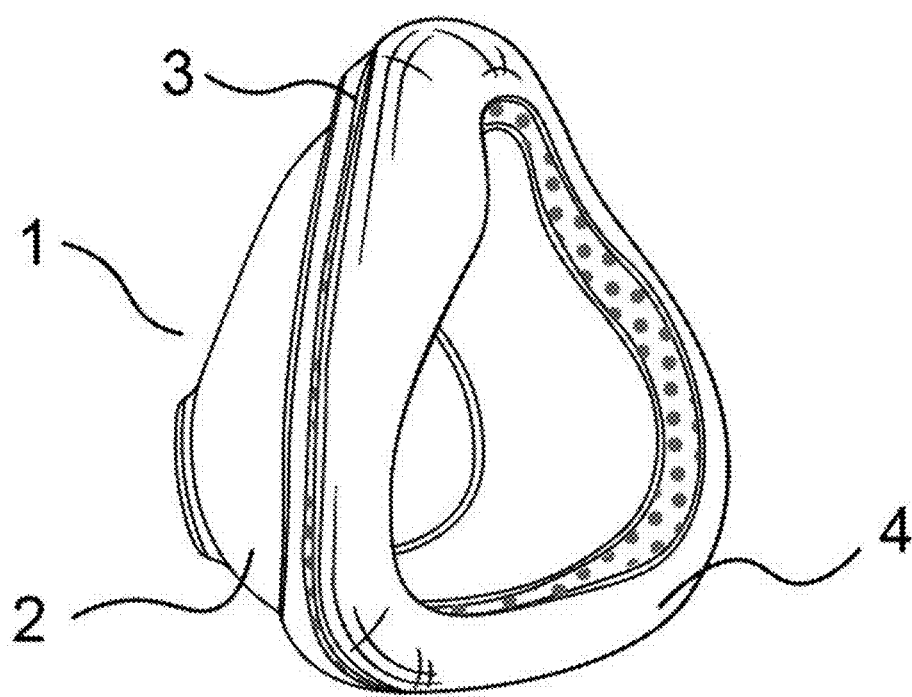
FIG. 7 is a schematic diagram of the structure of a patient interface pad with good comfort in accordance with an embodiment.

This embodiment describes a patient interface pad with good comfort, configured to deliver a pressurized airflow relative to the ambient air pressure to the entrance of an airway. The patient interface pad includes: a support section 2, including a first opening 21 in contact with other parts in the patient interface assembly (e.g., an elbow, an frame, etc.), connected to an elastic section 3; the elastic section 3, including a third opening 31 connected to the support section 2, a fourth opening 32 opposite the third opening 31, and a sidewall 33 that smoothly connects the third opening 31 and the fourth opening 32; and a comfort section 4, including a second surface 41 in contact with the elastic section 3 and a third surface 42 in contact with the face of the patient. Part of the side wall 33 of the elastic section 3 has a relatively gentle first surface 34 and the first surface is configured to be connected to the comfort section 4 through adhesive 8. The fourth opening 32 is configured to accommodate the nasal and oral airways or solely the nasal airway. The difference in this embodiment of the patient interface pad with good comfort from the patient interface pad in Embodiment 1 lies in: this further limits that the comfort section 4 includes a composite of foam material 6 and fabric 5. As shown in FIG. 7, the comfort section 4 includes a second surface 41 that contacts the elastic section 3 and a third surface 42 that contacts the face. In this embodiment, the comfort section 4 includes a composite of foam material 6 and fabric 5, where the second surface 41 of the comfort section is foam material 6, and the third surface 42 of the comfort section is fabric 5, with foam material 6 and fabric 5 being in a connected state. The foam material 6 in this embodiment has the same characteristics as in embodiment 3, and the fabric 5 has the same characteristics as in Embodiment 2. The fabric 5 is elastic, and changes in accordance with changes of a curvature of the foam material 6 when the fabric 5 is subjected to pressure. Foam material 6 and fabric 5 can be connected using adhesive 8, heat melting, pressure bonding, or by an intermediate layer (such as thermoplastic polyurethane material), and can also be connected by sewing, pressing, and other methods.

This embodiment provides a method for manufacturing a patient interface pad with good comfort. The difference from the patient interface pad in embodiment 1 lies in the amount of adhesive 8 being used. To ensure that adhesive 8 does not completely penetrate fabric 5 during production and can tightly bond with the elastic section 3, at least 0.05 g of adhesive 8 is used.

Embodiment 5

This embodiment describes a patient interface pad with good comfort, configured to deliver a pressurized airflow relative to the ambient air pressure to the entrance of an airway. The patient interface pad includes: a support section 2, including a first opening 21 in contact with other parts in the patient interface assembly (e.g., an elbow, an frame, etc.), connected to an elastic section 3; the elastic section 3, including a third opening 31 connected to the support section 2, a fourth opening 32 opposite the third opening 31, and a sidewall 33 that smoothly connects the third opening 31 and the fourth opening 32; and a comfort section 4, including a second surface 41 in contact with the elastic section 3 and a third surface 42 in contact with the face of the patient. Part of the side wall 33 of the elastic section 3 has a relatively gentle first surface 34 and the first surface is configured to be connected to the comfort section 4 through adhesive 8. The fourth opening 32 is configured to accommodate the nasal and oral airways or solely the nasal airway.

The difference in this embodiment of the patient interface pad with good comfort from the patient interface pad in Embodiment 1 lies in that the adhesive 8 is applied in a fully automatic manner, as specifically shown in FIGS. 22-25.

Step S1, firstly, based on ergonomics data and numerous comfort and air-tightness tests, obtain the patient interface pad of the elastic section 3 (and the elastic section 3 having an opening that meets the facial requirements of the patient) connected to the support section 2 (at this stage, the patient interface pad only having the support section 2 and the elastic section 3). The support section 2 includes a first opening 21 and a second opening 22, where the second opening 22 is configured to connect to the elastic section. They can be connected in a detachable or non-detachable manner. The first opening 21 is a fixed circular interface for connecting with external auxiliary devices (such as elbows, frames, etc.), and in other embodiments, it can be of other shapes. The elastic section 3 includes a third opening 31 connected to the support section 2, an opposite fourth opening 32, and a side wall 33 smoothly connecting the third and fourth openings. The fourth opening 32 can encircle the nasal airway or/and oral airway. Part of the side wall 33 of the elastic section 3 has a relatively gentle first surface 34;

Step S2, according to the size and shape of the first surface 34 of the elastic section 3 of the obtained patient interface pad, form the corresponding size and shape of the second surface 41 of the comfort section 4, and determine the size and shape of the third surface 42 of the comfort section 4 that contacts the face, based on the requirements of the respiratory assistance device. In the disclosure, a patient interface pad with the same support section 2 and elastic section 3 can be connected to different comfort sections 4, meaning that the first surface 34 of the elastic section 3 is configured to be connected to the comfort section 4 using adhesive 8. On the other hand, to achieve a close fit between the comfort section 4 and the face, the second surface 41 and the third surface 42 of the comfort section 4 form a continuous curved surface corresponding to the contours of the face. To ensure stability at the connection between the elastic section 3 and the support section 2, the wall thickness of the third opening 31 of the elastic section 3 is at least partly greater than the wall thickness of the fourth opening 32;

Step S3, fix the patient interface pad in the first container, where the first container can be fixture 93. The first container includes the receiving part 932 for placing the support section 2 of the patient interface pad or/and the elastic section 3, and the positioning part 931 that connects to the second container, along with a support bladder. The support bladder is designed to automatically inflate and support the elastic section 3 after the patient interface pad is fixed;

Step S4, finish the pretreatment of cleaning the patient interface pad and the comfort section 4 to ensure the material surfaces are clean and tidy, free of oil stains, dust, wrinkles, and other contaminants that could affect the quality of adhesion;

Step S5, fix comfort section 4 that has finished the pretreatment of cleaning in the second container, where the second container can be fixture 94. The second container includes the receiving part 942 for placing the comfort section 4, and the positioning part 941 that connects to the first container;

Step S6, move the first container that has finished the pretreatment of cleaning beneath the adhesive application equipment, as shown in FIGS. 9-10. The adhesive application equipment automatically applies adhesive 8 to a portion of the first surface 34 of the elastic section 3 or entirely cover the first surface 34, following a preset program along a designated path. The glue release path of the adhesive application equipment is a complete and continuous ring. The number of paths is chosen based on the material of adhesive 8 but should be at least one. The area where adhesive 8 is applied does not exceed the area of the second surface 41 of the comfort section 4.

Step S7, connect the first container and the second container according to their corresponding structures, place the adhesive 8 between the elastic section 3 and the comfort section 4, and let it set aside for curing. Once the connection is complete, remove the patient interface pad 1 from the first container and return the empty first container to the material box.

In another embodiment, in Step S6, adhesive 8 is applied to a portion of the second surface 41 of the comfort section 4. Through a designed program, adhesive 8 is automatically applied to a portion of the second surface 41 of the comfort section 4, or entirely covers the second surface 41, using the adhesive application equipment following a path. The glue application path of the adhesive application equipment is a complete and continuous ring. The number of paths can be chosen based on the material of adhesive 8 but should be at least one. The range of adhesive 8 application does not exceed the area of the second surface 41 of the comfort section 4.

Implementing the patient interface pad and its manufacturing method in the disclosure provides at least the following beneficial effects:

1. Reduced R&D Cycle: Most patient interface pads on the market, aiming to provide a more comfortable user experience for patients, focus on researching and designing the curvature of the elastic section to better conform to the curves of the face. Due to the complex three-dimensional characteristics of the human face, the design process requires reference to a large amount of ergonomics-related data. This involves extensive testing, verification, and adjustments for comfort and airtightness. Furthermore, the production of the elastic section, owing to the material's curing requirements, typically has a longer production cycle compared to the supportive parts. In this approach, a. R&D personnel need to create a three-dimensional model of the patient interface pad. Based on this established three-dimensional model, they proceed with mold making (this process typically takes 30-50 days). Only after obtaining the mold can the production of the elastic section begin. b. Due to the elastic section typically being made of thermoplastic elastomer materials, its production involves several steps: preparation of raw materials (usually supplied in pellet form), pre-treatment (the material needs to experience pre-treatment steps of drying and mixing of raw materials to ensure the quality and stability of material), injection of raw materials (using the prepared mold for injection molding), and cooling and curing treatment (curing time often takes several days). c. The research and development personnel need to conduct numerous comfort and air-tightness tests on the produced products, then adjust the three-dimensional models, and repeat these steps multiple times to develop a relatively comfortable patient interface pad. The preparation method of this disclosure uses the same patient interface pad, and by connecting different materials to the elastic section of the patient interface pad, through the research and the design of more readily obtainable materials such as foam material (foam molding) and fabric (textile process) that are materials which are comfortable and capable of deformation. This approach shortens the design process for optimizing the comfort of the patient interface pad, thereby realizing a faster provision of a more comfortable experience for the patient. In this method, a. Prepare a patient interface pad suitable for the facial shape of the majority of people in the early stage, and at the same time, design comfortable materials, and produce a variety of forms of the comfort section through relatively simple operations such as cutting and trimming the comfortable materials. b. Connect the patient interface pad with the comfort section by adhesive through a fix connection and then multiple types of patient interface pads contacting different areas of the user's face can be obtained. By producing patient interface pads with varying degrees of comfort in this way, it is possible to eliminate redesign steps in the production of thermoplastic elastomers, reducing research and development time by three months or more. Additionally, it enables the rapid design of new types of the comfort section based on market trends or user preferences, allowing the patient interface pads to meet the comfort needs of different patients, therefore, the product can be put on the market more quickly and effectively, by creating a series of products.

2. Modular Preparation Method: In the current patient interface pad market, most patient interface pads are configured to match with a fixed frame component to form a complete patient interface assembly for use. However, these interface pads cannot meet the needs of different patients. For producers, designing different patient interface pads within the same patient interface assembly is undoubtedly a waste of cost: a. It requires producing support sections with the same function but different structures, wasting materials;

b. The elastic sections are usually made of thermoplastic elastomers, which typically have slower production times and higher defect rates than materials like plastic. Considering these two points, the optimized design of patient interface pads demands high requirements in terms of material costs and time costs. In the preparation method of this disclosure, a modular approach is used. Innovatively, comfortable materials like foam material and fabric are fixedly connected to the patient interface pad. This method allows for the provision of a variety of patient interface pads with good comfort for the market. a. Producers only need to manufacture one universal patient interface pad, eliminating the need to waste materials on multiple design validations of the elastic section for air-tightness and comfort. b. In this manufacturing method, since the more complex parts of the product (the support section and the elastic section) are confirmed, it is only necessary to design different types of the comfort section to meet patient needs. This approach makes quality control of the components easier, stabilizes the overall product quality control, and saves overall production time. It also significantly reduces the defect rate. c. The support section and the elastic section, as the basic parts of the patient interface pad, have increased reusability, which can reduce the adverse environmental impact of excessive industrial products.

3. Supply Aspect: Currently, the supply of ordinary patient interface pads in the market, from the perspective of the product supply chain, requires warehouses to be equipped with different types of patient interface pads to meet the varying needs of different patients for shipment, which demands high storage costs (material costs, space costs, etc.). For the product suppliers, factories need to be equipped with different types of production molds for patient interface pads to prepare the relatively complex patient interface pads, resulting in high costs in terms of mold expenses and material consumption. In the face of major public health events such as COVID-19, there has been a huge challenge to the supply of medical materials. The production cycle of ventilators, which is already not short, has faced a global shortage. This has led to a widespread situation of demand outstripping supply among ventilator manufacturers. The reason lies in the numerous materials and processes required for ventilator systems, with the majority of raw materials being in short supply due to the obstacles caused by the pandemic. By using a modular design approach, a. Producers only need to prepare one model for producing patient interface pads and store a large number of the same patient interface pads in the warehouse. During preparation and assembly of goods, products can be quickly shipped out by fixing the comfort section to the elastic section of the patient interface pad with adhesive according to customer needs. This significantly reduces storage and production costs, reduces material waste, and enhances the flexibility of the production line; and uses simpler, more readily available materials, without the need for extensive imports or special materials, to ensure the stability of the supply chain. b. in this manufacturing method, since there are many fundamentally similar parts in the product, the same production processes, tools, and equipment can be adopted, which reduces production and manufacturing costs. Different modular components can be manufactured simultaneously and can undergo independent testing and inspection. This allows for quick repairs of components that encounter a problem, making quality control of the components easier. It stabilizes the overall product quality control, saves time in overall production, and significantly reduces the defect rate. c. The support section and the elastic section, as the foundational parts of the patient interface pad, have increased reusability, which can reduce the adverse environmental impact of excessive industrial products. d. Materials like foam material and fabric, compared to thermoplastic elastomers, are easier to shape into the desired form, allowing for quicker iterations in the product supply.

4. Providing Users with Better Patient Interface Pads: Besides offering users a variety of patient interface pads, more importantly: a. Compared to existing patient interface pads that use silicone seals alone, fabric, foam material, or their composite are more breathable than silicone. They can provide varying degrees of comfortable contact surfaces. Additionally, they can absorb oils and sweat produced during prolonged use, keeping the face dry and avoiding skin sensitivity issues, as well as reducing the displacement of silicone because of contact with sweat or oils. b. The adhesive used in this method is non-toxic and harmless, with moderate tensile strength, and with appropriate softness and hardness after curing, and it appears transparent or semi-transparent. Furthermore, adhesive does not damage the surface of the elastic section or produce harmful waste. c. Due to lower production costs, the purchasing cost for patients is also reduced, making it more affordable for users. Users are able to enjoy and experience a wider variety of patient interface pads, allowing them to choose the most suitable one.

The technical features of the embodiments described above can be combined in any manner. To keep the description concise, not all possible combinations of the technical features in the above embodiments are described. However, as long as there is no contradiction in these combinations of technical features, they should be considered within the scope of this specification.

The embodiments described above only represent a few of the possible implementation disclosure and are described in specific and detailed terms, but should not be construed as limiting the scope of the patent for the disclosure. It should be noted that, for those skilled in the art, various modifications and improvements can be made without departing from the concept of this disclosure, and these are also within the scope of protection of this disclosure. Therefore, the scope of protection of the patent for this disclosure should be determined by the attached claims.

It must be noted that as used herein and in the appended claims, the singular forms "a", "an", and "the" include their plural equivalents, unless the context clearly dictates otherwise.

The invention claimed is:

1. A patient interface pad configured to seal and deliver a pressurized airflow relative to an ambient air pressure to an entrance of an airway, the patient interface pad comprising:
   a support section, comprising a first opening and a second opening, wherein the second opening is configured to connect to an elastic section;
   the elastic section, comprising a third opening connectable to the support section, a fourth opening opposite the third opening, and a side wall that connects the third opening and the fourth opening, wherein part of the side wall includes a first surface, and the first surface is configured to connect to a comfort section, wherein the fourth opening is configured to contact an area around a nasal passage and oral passage, or only the nasal passage of a patient;
   the comfort section, including a second surface in contact with the elastic section and a third surface that is configured to contact a face of the patient, wherein the comfort section includes foam material, wherein the foam material is a porous material; and wherein, the first surface of the elastic section and the second surface of the comfort section are connectable along a common contact portion along a periphery of the first surface of the elastic section by an adhesive, and the adhesive has one or more of the following characteristics:

a. an amount of the adhesive used being at least 0.05 g;
b. a density range of at or between 0.3 to 3 g/cm$^3$;
c. a temperature resistance range of at or between −55° C. to 200° C.;
d. a tensile strength being greater than or equal to 0.5 MPa; and
e. the adhesive being applied in a continuous path and a perimeter of the path being not less than a perimeter of the fourth opening.

2. The patient interface pad according to claim 1, wherein a material of the support section includes polycarbonate, polypropylene, polyethylene, or thermoplastic elastomer with a hardness of Shore A at or between 30 to 80, and the second opening of the support section and the third opening of the elastic section are connected and formed by molding or co-molding.

3. The patient interface pad according to claim 1, wherein the first surface of the elastic section and the second surface of the comfort section, when connected, have a same curvature in the common contact portion where they come into contact with each other, and the third surface of the comfort section is configured to partially conform to a curve of the face of the patient during use.

4. The patient interface pad according to claim 1, wherein the foam material has a continuous three-dimensional shape with a width-to-thickness ratio at or between 0.1 to 30.

5. A patient interface pad configured to seal and deliver a pressurized airflow relative to an ambient air pressure to an entrance of an airway, the patient interface pad comprising:

a support section, comprising a first opening and a second opening, wherein the second opening is configured to connect to an elastic section;

the elastic section, comprising a third opening connectable to the support section, a fourth opening opposite the third opening, and a side wall that connects the third opening and the fourth opening, wherein part of the side wall includes a first surface, and the first surface is configured to connect to a comfort section;

the comfort section, including a second surface in contact with the elastic section and a third surface that is configured to contact a face of a patient, wherein the comfort section includes foam material, wherein the foam material is a porous material; and wherein, the first surface of the elastic section and the second surface of the comfort section are connectable by an adhesive, and the adhesive has one or more of the following characteristics:

a. an amount of the adhesive used being at least 0.03 g;
b. a hardness after curing being greater than or equal to Shore A 15;
c. a temperature resistance range of at or between −55° C. to 200° C.;
d. an area where the adhesive is applied not exceeding the second surface of the comfort section; and
e. a colloidal state before curing being liquid or semi-flowing.

6. The patient interface pad according to claim 5, wherein the fourth opening is configured to contact an area around a nasal passage and oral passage, or only the nasal passage of the patient.

7. The patient interface pad according to claim 5, wherein a material of the support section includes polycarbonate, polypropylene, polyethylene, or thermoplastic elastomer with a hardness of Shore A at or between 30 to 80, and the second opening of the support section and the third opening of the elastic section are connected and formed by molding or co-molding.

8. The patient interface pad according to claim 5, wherein the foam material has a continuous three-dimensional shape with a width-to-thickness ratio at or between 0.1 to 30.

9. A patient interface pad configured to seal and deliver a pressurized airflow relative to an ambient air pressure to an entrance of an airway, the patient interface pad comprising:

a support section, comprising a first opening and a second opening, wherein the second opening is configured to connect to an elastic section;

the elastic section, comprising a third opening connectable to the support section, a fourth opening opposite the third opening, and a side wall that connects the third opening and the fourth opening, wherein part of the side wall includes a first surface, and the first surface is configured to connect to a comfort section;

the comfort section, including a second surface in contact with the elastic section and a third surface that is configured to contact a face of a patient, wherein the comfort section includes foam material, wherein the foam material is a porous material; and wherein, the first surface of the elastic section and the second surface of the comfort section are connectable along a common contact portion along a periphery of the first surface of the elastic section by an adhesive.

10. The patient interface pad according to claim 9, wherein the adhesive has one or more of the following characteristics:

a. an amount of the adhesive used being at least 0.05 g;
b. a density range of at or between 0.3 to 3 g/cm$^3$;
c. a temperature resistance range of at or between −55° C. to 200° C.;
d. a tensile strength being greater than or equal to 0.5 MPa; and
e. the adhesive being applied in a continuous path and a perimeter of the path being not less than a perimeter of the fourth opening.

11. The patient interface pad according to claim 9, wherein the fourth opening is configured to contact an area around a nasal passage and oral passage, or only the nasal passage of the patient.

12. The patient interface pad according to claim 9, wherein a material of the support section includes polycarbonate, polypropylene, polyethylene, or thermoplastic elastomer with a hardness of Shore A at or between 30 to 80.

13. A patient interface pad configured to seal and deliver a pressurized airflow relative to an ambient air pressure to an entrance of an airway, the patient interface pad comprising:

a support section, comprising a first opening and a second opening, wherein the second opening is configured to connect to an elastic section;

the elastic section, comprising a third opening connectable to the support section, a fourth opening opposite the third opening, and a side wall that connects the third opening and the fourth opening, wherein part of the side wall includes a first surface, and the first surface is configured to connect to a comfort section, wherein the fourth opening is configured to contact an area around a nasal passage and oral passage, or only the nasal passage of a patient;

the comfort section, including a second surface in contact with the elastic section and a third surface that is configured to contact a face of the patient, wherein the comfort section includes foam material, wherein the foam material is a porous material; and wherein, the first surface of the elastic section and the second surface of the comfort section are connectable along a common contact portion along a periphery of the first surface of the elastic section by an adhesive.

14. The patient interface pad according to claim 13, wherein a roughness average value of the third surface of the comfort section is at or between 0.2 to 10 micrometers.

15. The patient interface pad according to claim 13, wherein the adhesive has one or more of the following characteristics:
   a. an amount of the adhesive used being at least 0.03 g;
   b. a hardness being greater than or equal to Shore A 15;
   c. a density of at least 0.3 g/cm$^3$; and
   d. a color after curing being transparent or translucent.

16. The patient interface pad according to claim 13, wherein the adhesive is configured to be applied in a continuous path and a perimeter of the path is not less than a perimeter of the fourth opening.

* * * * *